US010736841B2

(12) United States Patent
Padilla et al.

(10) Patent No.: US 10,736,841 B2
(45) Date of Patent: Aug. 11, 2020

(54) BEPOTASTINE COMPOSITIONS

(75) Inventors: Angel Padilla, Aliso Viejo, CA (US); George Baklayan, Huntington Beach, CA (US)

(73) Assignee: BAUSCH & LOMB INCORPORATED, Rochester, NY (US)

(*) Notice: Subject to any disclaimer, the term of this patent is extended or adjusted under 35 U.S.C. 154(b) by 349 days.

(21) Appl. No.: 13/462,466

(22) Filed: May 2, 2012

(65) Prior Publication Data

US 2012/0255544 A1 Oct. 11, 2012

Related U.S. Application Data

(62) Division of application No. 13/505,438, filed as application No. PCT/US2012/020028 on Jan. 3, 2012, now abandoned.

(60) Provisional application No. 61/429,721, filed on Jan. 4, 2011.

(51) Int. Cl.
| | | |
|---|---|---|
| *A61K 9/10* | (2006.01) | |
| *A61K 9/12* | (2006.01) | |
| *A61K 31/444* | (2006.01) | |
| *A61K 45/06* | (2006.01) | |
| *A61K 47/18* | (2017.01) | |
| *A61K 47/38* | (2006.01) | |
| *A61K 9/00* | (2006.01) | |

(52) U.S. Cl.
CPC ............. *A61K 9/10* (2013.01); *A61K 9/0043* (2013.01); *A61K 9/12* (2013.01); *A61K 31/444* (2013.01); *A61K 45/06* (2013.01); *A61K 47/186* (2013.01); *A61K 47/38* (2013.01)

(58) Field of Classification Search
CPC .... A61K 31/4196; A61K 47/10; A61K 47/20; A61K 9/0014
See application file for complete search history.

(56) References Cited

U.S. PATENT DOCUMENTS

| | | | |
|---|---|---|---|
| 5,622,724 A | 4/1997 | Bryce-Smith | |
| 5,976,573 A | 11/1999 | Kim | |
| 6,565,832 B1 | 5/2003 | Haslwanter et al. | |
| 6,780,398 B1 | 8/2004 | Akutsu et al. | |
| 2003/0185763 A1 | 10/2003 | Haslwanter et al. | |
| 2005/0107429 A1* | 5/2005 | Higashiyama | 514/318 |
| 2005/0112199 A1 | 5/2005 | Padval et al. | |
| 2006/0110331 A1 | 5/2006 | Dang et al. | |
| 2008/0254029 A1 | 10/2008 | Yanni et al. | |
| 2009/0312724 A1* | 12/2009 | Pipkin et al. | 604/294 |
| 2009/0324699 A1* | 12/2009 | Preswetoff-Morath et al. | 424/450 |
| 2009/0325917 A1 | 12/2009 | Lulla et al. | |
| 2012/0225905 A1* | 9/2012 | Padilla et al. | 514/318 |

FOREIGN PATENT DOCUMENTS

| | | |
|---|---|---|
| CN | 1222852 A | 7/1999 |
| JP | H11-511758 | 10/1999 |
| JP | 2003-510275 | 3/2003 |
| JP | 2004-532871 | 10/2004 |
| JP | 2005-511724 | 4/2005 |
| JP | 2007-529525 | 10/2007 |
| JP | 2008-521812 | 6/2008 |
| JP | 2009-544665 | 12/2009 |
| JP | 2010195716 A | 9/2010 |
| WO | WO 98/29409 | 7/1998 |
| WO | 03101434 A2 | 12/2003 |
| WO | 2004/011001 | 2/2004 |
| WO | 2005030132 A2 | 4/2005 |
| WO | 2007026151 A1 | 3/2007 |
| WO | 2008127975 A2 | 10/2008 |
| WO | WO 2008/123701 | 10/2008 |
| WO | WO 2009/075504 | 6/2009 |
| WO | WO 2010/026129 | * 3/2010 |

OTHER PUBLICATIONS

"Structure-Activity Relationship and Drug Design." Remington's Pharmaceutical Sciences (Sixteenth Edition). Mack Publishing, 1980, pp. 420-425.*
Mehta et al. Novel nasal in situ gelling systm for treatment of sinusitis. Indian J. Pharm. Sci. 2009, Nov.-Dec. 71(6): 721-722.*
Methocel Cellulose Ethers Technical Handbook. Form No. 192-01062-0902 AMS published Sep. 2002.*
Flonase Prescribing Information (GlaxoSmithKline, Mar. 2004, hereinafter referred to as Flonase).*
Bepreve® Prescribing Information (Bausch&Lomb Inc., revised Aug. 2009.*
International Search Report (8 pages) and Written Opinion (10 pages) of the World Intellectual Property Organization for PCT/US2012/020028, dated Aug. 27, 2012.
International Preliminary Report on Patentability for PCT/US2012/020028, dated Jul. 18, 2013 (12 pages).
Hampel et al. Double-blind, placebo-controlled study study of azelastine and fluticasone in a single nasal spray delivery device. Ann. Allergy Asthma. Immunol. 105 (2010) 168-173.
LaForce et al. Evaluation of olopatadine hydrochloride nasal spray, 0.6%, used in combination with an intranasal corticosteroid in seasonal allergy rhinitis. Allergy Asthma Proc 31 (2010) 132-140.
Williams et al., "Non-clinical pharmacology, pharmacokinetics, and safety findings for the antihistamine bepotastine pesilate", Curr Med Res Opin. Oct. 2010;26(10):2329-38.
Opthalmology Times (http://opthalmologytimes.modernmedicine.com, publish date Aug. 4, 2010.
Japan Patent Office, Official Action dated Jun. 10, 2014 in Application No. 2013-532933 and translation thereof.
MEDA Pharmaceuticals, "Astelin Nasal Spray Product Information" Rev. Jan. 9.
State Intellectual Property Office of China, Official Action dated May 5, 2014 in Invention No. 201180048106.3 and English translation thereof.

(Continued)

*Primary Examiner* — Marcos L Sznaidman
*Assistant Examiner* — Rayna Rodriguez
(74) *Attorney, Agent, or Firm* — Thompson Hine LLP

(57) ABSTRACT

Novel compositions including bepotastine besilate and a corticosteroid are provided, compositions including at least about 0.008% w/v benzalkonium chloride, and compositions including hydroxypropylmethyl cellulose E15 LV.

19 Claims, No Drawings

(56) References Cited

OTHER PUBLICATIONS

Guo et al., "The effect of formulation variables and breathing patterns on the site of nasal deposition in an anatomically, correct model", Pharm Res. Nov. 2005;22(11):1871-8. Epub Aug. 16, 2005.
Torkildsen et al, "Bepotastine besilate ophthalmic solution for the relief of nonocular symptoms provoked by ,conjunctival allergen challenge", Ann Allergy Asthma Immunol. Jul. 2010;105(1):57-64.
International Bureau of WIPO, International Preliminary Report on Patentability issued Apr. 9, 2013 for International Application No. PCT/US2011/055011.
International Bureau of WIPO, International Search Report and Written Opinion issued in International Application No. PCT/US2011/055011 dated Apr. 10, 2012.
The Free Dictionary, "Propellant", obtained from the internet May 22, 2017 at http://www.thefreedictionary.com/propellant.
Oxford Dictionary, "Spray" obtained from the internet May 22, 2017 at https://en.oxforddictionaries.com/definition/spray.
Exhibit A. FMC BioPolymer, AVICEL® for Suspsensions (2014), available at http://www.fmcbiopolymer.com/Pharmaceutical/Products/Avicelforsuspensions.aspx, 1 page.
Exhibit B. FMC BioPolymer, Material Safety Data Sheet AVICEL® CL 611 Stabilizer, approved Jan. 9, 2010, 8 pages.
Exhibit C. Dow Chemical Company, METHOCEL Cellulose Ethers in Aqueous Systems for Tablet Coating, Jan. 2003, 5 pages.
Exhibit D. FMC BioPolymer, Product Specification Bulletin AVICEL® CL 611, Feb. 2009. 2 pages.
Hardy et al., "Intranasal drug delivery by spray and drops", J Pharm Pharmacol, May 1985; 37(5), pp. 294-7.

* cited by examiner

BEPOTASTINE COMPOSITIONS

This application is a Divisional of U.S. patent application Ser. No. 13/505,438 filed May 1, 2012, which is a National Phase entry of International Application No. PCT/US2012/020028, filed Jan. 3, 2012, which claims priority to U.S. Provisional Application Serial No. 61/429,721 filed Jan. 4, 2011 which are expressly incorporated by reference herein in their entirety.

BACKGROUND

Bepotastine, (+)-(S)-4-[4-[(4-chlorophenyl)(2-pyridyl)methoxy]piperidino]butyric acid, is a non-sedating, highly selective antagonist of the histamine H1 receptor. It has a stabilizing effect on mast cells, and it suppresses the migration of eosinophils into inflamed tissues. It has three mechanisms of action: mast cell stabilizer, histamine antagonist, and modulator/inhibitor of eosinophils. Bepotastine and pharmacologically acceptable salts thereof have an antihistaminic action and an antiallergic action. They are also characterized in that secondary effects such as stimulation or suppression of the central nerve often seen in the case of conventional antihistaminic agents can be minimized, and can be used as effective pharmaceutical agents for the treatment of human and animals (PCT Patent Publication No. WO98/29409).

Bepotastine besilate has been approved in Japan for systemic use in the treatment of allergic rhinitis since 2000 and urticaria/pruritus since 2002. It is marketed in Japan by Mitsubishi Tanabe Pharma Corporation (formerly Tanabe Seiyaku Co., Ltd.) under the brand name TALION®. ISTA Pharmaceuticals' eye drop formulation of bepotastine besilate, BEPREVE® (bepotastine besilate ophthalmic solution) 1.5% w/v, was approved by the U.S. Food and Drug Administration (FDA) in September 2009 for the treatment of ocular itching associated with allergic conjunctivitis.

DETAILED DESCRIPTION THE INVENTION

Provided herein, inter alia, are novel compositions comprising bepotastine as a free base, pharmaceutically acceptable salt, solvate, or physiologically functional derivative thereof, and at least one corticosteroid as a free form, pharmaceutically acceptable salt, solvate, or physiologically functional derivative thereof, the composition which is effective for suppressing nasal inflammatory conditions.

The present invention relates to the following.
[1] A pharmaceutical composition comprising at least one corticosteroid as a free form, pharmaceutically acceptable salt, solvate, or physiologically functional derivative thereof, and bepotastine as a free base, pharmaceutically acceptable salt, solvate or physiologically functional derivative thereof, the bepotastine at a concentration from 0.5% w/v to 8.00% w/v inclusive, with at least one pharmaceutically compatible excipient, the composition formulated as a nasal spray.
[2] The composition of [1] above wherein the bepotastine concentration is from 2.00% w/v to 4.00% w/v inclusive.
[3] The composition of any of [1]-[2] above wherein the excipient is a viscosity enhancing agent and is hydroxypropylmethyl cellulose (HPMC).
[4] The composition of [3] above wherein the concentration of the viscosity enhancing agent is from 0.01% w/v-1.00% w/v.
[5] The composition of any of [1]-[4] above further comprising a preservative.
[6] The composition of [5] above wherein the preservative is benzalkonium chloride.
[7] The composition of any of [5]-[6] above wherein the concentration of the preservative is from 0.002% w/v-0.200% w/v.
[8] The composition of any of [1]-[7] above further comprising at least one pharmaceutically compatible buffer, a tonicity agent, a chelating agent, a suspending agent, and an optional taste-masking agent.
[9] The composition of [8] above wherein the pharmaceutically compatible buffer is each of a phosphate buffer and a citrate buffer.
[10] The composition of [9] above wherein the phosphate buffer is dibasic sodium phosphate heptahydrate and the citrate buffer is citric acid monohydrate.
[11] The composition of any of [8]-[10] above wherein the concentration of the buffer is 0.10% w/v-1.00% w/v.
[12] The composition of [8] above wherein the tonicity agent is sodium chloride.
[13] The composition of any of [8] or [12] above wherein the concentration of the tonicity agent is 0.1% w/v-0.9% w/v.
[14] The composition of [8] above wherein the chelating agent is ethylenediamine tetraacetic acid.
[15] The composition of any of [8] or [14] above wherein the concentration of the chelating agent is 0.005% w/v-0.100% w/v.
[16] The composition of [1] above wherein the excipient is a suspending agent comprising a blend of microcrystalline cellulose and carboxymethyl cellulose (AVICEL®) and/or polyoxyethylene (20) sorbitan monooleate (polysorbate 80).
[17] The composition of [1] above wherein the excipient is a suspending agent comprising HPMC, AVICEL®, and polysorbate 80.
[18] The composition of any of [16]-[17] above wherein the concentration of the suspending agent is 0.5% w/v-2.5% w/v for AVICEL® and is 0.005% w/v-0.050% w/v for polysorbate 80.
[19] The composition of any of [16]-[18] above wherein AVICEL® is AVICEL® CL-611.
[20] The composition of [8] above wherein the optional taste-making agent is (tri)sodium citrate, sodium citrate, sodium chloride, sodium bicarbonate, a polyol sweetener, a high intensity sweetener, and/or a flavoring agent.
[21] The composition of any of [8] or [20] above wherein the optional taste-masking agent is sucralose.
[22] The composition of any of [8], [20], or [21] above wherein the concentration of the optional taste making agent is 0%-1.00% w/v.
[23] The composition of any of [1]-[22] above where the pharmaceutically acceptable bepotastine salt is besilate.
[24] The composition of any of [1]-[23] wherein the corticosteroid concentration is from 0.01% w/v to 1% w/v inclusive, and the corticosteroid is selected from the group consisting of beclomethasone, beclomethasone dipropionate, mometasone furoate monohydrate, fluticasone propionate, fluticasone furoate, triamcinolone, triamcinolone acetonide, budesonide, budesonide free acid, ciclesonide, beclomethasone sodium, dexamethasone sodium, prednisolone acetate, and mixtures thereof.
[25] A pharmaceutical composition comprising bepotastine besilate and a corticosteroid free form, pharmaceutically acceptable salt, solvate, or physiologically functional derivative thereof, dibasic sodium phosphate heptahydrate, sodium chloride, edetate disodium, benzalkonium chloride, and one of either: a blend of microcrystalline cellulose and carboxymethyl cellulose (AVICEL®) and/or polyoxyethylene (20) sorbitan monooleate (polysorbate 80), or hydroxypropylmethyl cellulose (HPMC), citric acid monohydrate, and a taste making agent.

[26] The composition of [25] above wherein the concentration of bepotastine besilate is 0.5% w/v to 8.00% w/v; the concentration of corticosteroid is 0.01% w/v to 1.00% w/v; the concentration of dibasic sodium phosphate heptahydrate is 0.10% w/v to 1.00% w/v; the concentration of sodium chloride is 0.9% w/v with 0.5% bepotastine, 0.4% w/v with 2.00%-3.00% bepotastine, 0.3% w/v with 4.00% bepotastine, 0.2% w/v with 6.00% bepotastine, 0.1% w/v with 8.00% bepotastine; the concentration of edetate disodium is 0.005% w/v to 0.100% w/v; the concentration of benzalkonium chloride is 0.002% w/v to 0.200% w/v; and if used, the concentration of AVICEL® CL-611 is 0.5% w/v to 2.5% w/v, and the concentration of polysorbate 80 is 0.005% w/v to 0.050% w/v; or if used, the concentration of HPMC is 0.01% w/v to 1.00% w/v, the concentration of citric acid monohydrate is 0.10% w/v to 1.00% w/v, and the concentration of the Paste-making agent is 0.01% w/v to 1.00% w/v.

[27] The composition of [25] above wherein the concentration of bepotastine besilate is 4.00% w/v, the concentration of corticosteroid is 0.05% w/v, the concentration of dibasic sodium phosphate heptahydrate is 0.70% w/v, the concentration of sodium chloride is 0.30% w/v, the concentration of edetate disodium is 0.020% w/v, the concentration of benzalkonium chloride is 0.020% w/v, and if used, the concentration of AVICEL® CL-611 is 2.00% w/v and the concentration of polysorbate 80 is 0.015% w/v; or if used, the concentration of HPMC E15 LV is 0.10% w/v, the concentration of citric acid monohydrate is 0.10% w/v, and the taste-masking agent is sucralose and the concentration thereof is 0.10% w/v.

[28] The composition of any of [25]-[27] above lacking substantial impurities.

[29] The composition of any of [25]-[28] above optionally containing sorbitol.

[30] The composition of any of [25]-[29] above having pH 4-9.

[31] The composition of any of [25]-[30] above containing AVICEL® CL-611 and polysorbate 80 and having pH 6.4, or containing HPMC E15 LV, citric acid monohydrate, and a taste making agent and having pH 6.8.

[32] Use of the composition of any of [25]-[31] above formulated for nasal administration to treat at least one of rhinitis, mucosal inflammation associated with rhinitis, sinusitis, rhinosinusitis, and symptoms associated with rhinitis, mucosal inflammation associated with rhinitis, sinusitis, or rhinosinusitis.

[33] The use of [32] above wherein rhinitis includes acute rhinitis, chronic rhinitis, allergic rhinitis, seasonal allergic rhinitis, perennial allergic rhinitis, vasomotor rhinitis, infectious rhinitis, and atrophic rhinitis.

[34] The use of any of [32]-[33] above wherein the composition is formulated as a nasal spray, nasal drops, nasal droplets, or combinations thereof.

[35] The use of any of [32]-[34] above wherein the composition is nasally administered by a metered dose inhaler (MDI).

[36] The use of [35] above wherein the MDI is any of a breath-actuated MDI, a dry powder inhaler, a spacer/holding chambers in combination with a MDI, and a nebulizer.

[37] The use of any of [35]-[36] above wherein the composition is in a wet spray formulation or a dry spray formulation.

[38] The use of any of [32]-[35] above wherein the composition is nasally administered by a metered dose plunger spray pump.

[39] A method of treating at least one of rhinitis, mucosal inflammation associated with rhinitis, sinusitis, rhinosinusitis, and symptoms associated with rhinitis, mucosal inflammation associated with rhinitis, sinusitis, or rhinosinusitis in a patient in need of such treatment, the method comprising nasally administering a pharmaceutical composition comprising a corticosteroid as a free form, pharmaceutically acceptable salt, solvate or physiologically functional derivative thereof and bepotastine as a free base, pharmaceutically acceptable salt, solvate, or physiologically functional derivative thereof at a concentration ranging from 0.5% w/v to 8.00% w/v in aqueous solution to the patient in need thereof, in a dose regimen effective to treat at least one of rhinitis, mucosal inflammation associated with rhinitis, sinusitis, rhinosinusitis, and symptoms associated with rhinitis, mucosal inflammation associated with rhinitis, sinusitis, or rhinosinusitis.

[40] The method of [39] above wherein bepotastine in the composition administered is at a concentration ranging from 2.00% w/v to 4.00% w/v and corticosteroid in the composition administered is at a concentration ranging from 0.01% w/v to 1% w/v.

[41] The method of any of [39]-[40] above wherein administration is from 1 time a day to 4 times a day.

[42] The method of [41] above wherein bepotastine in the composition administered is at a concentration of either 3.00% w/v or 4.00% w/v and administration is 1 time a day.

[43] The method of [41] above wherein bepotastine in the composition administered is at a concentration of either 3.00% w/v or 4.00% w/v and administration is at more than 12 hour intervals.

[44] The method of any of [41]-[43] above wherein the dose regimen is effective to treat allergic rhinitis.

[45] The method of any of [39]-[44] above wherein the composition administered comprises
    dibasic sodium phosphate heptahydrate at a concentration of 0.10% w/v to 1.00% w/v;
    sodium chloride at a concentration of 0.9% w/v with 0.5% bepotastine, 0.4% w/v with 2.00%-3.00% bepotastine, 0.3% w/v with 4.00% bepotastine, 0.2% w/v with 6.00% bepotastine, 0.1% w/v with 8.00% bepotastine;
    edetate disodium at a concentration of 0.005% w/v to 0.100% w/v;
    benzalkonium chloride at a concentration of 0.002% w/v to 0.200% w/v; and one of either:
    a blend of microcrystalline cellulose and carboxymethyl cellulose (AVICEL®) at a concentration of 0.5% w/v to 2.5% w/v and polyoxyethylene (20) sorbitan monooleate (polysorbate 80) at a concentration of 0.005% w/v to 0.050% w/v, or
    HPMC E15 LV at a concentration of 0.01% w/v to 1.00% w/v, citric acid monohydrate at a concentration of 0.10% w/v to 1.00% w/v, and a taste-making agent at a concentration of 0.01% w/v to 1.00% w/v.

[46] The method of any of [39]-[44] above wherein the composition administered comprises dibasic sodium phosphate heptahydrate at a concentration of 0.70% w/v, sodium chloride at a concentration of 0.30% w/v, edetate disodium at a concentration of 0.020% w/v, benzalkonium chloride at a concentration of 0.020% w/v, and one of either:
    AVICEL® at a concentration of 2.00% w/v and polysorbate 80 at a concentration of 0.015% w/v, or HPMC E15 LV at a concentration of 0.10% w/v, citric acid monohydrate at a concentration of 0.10% w/v, and sucralose at a concentration of 0.10% w/v.

[47] The method of any of [39]-[46] above wherein the pharmaceutically acceptable salt of bepotastine is besilate.

[48] The method of any of [45]-[46] above wherein AVICEL® is AVICEL® CL-611.

[49] The method of any of [39]-[48] above wherein the corticosteroid is selected from the group consisting of beclomethasone, beclomethasone dipropionate, mometasone furoate monohydrate, fluticasone propionate, fluticasone furoate, triamcinolone, triamcinolone acetonide, budesonide, budesonide free acid, ciclesonide, beclomethasone sodium, dexamethasone sodium, prednisolone acetate, and mixtures thereof.

[50] A kit comprising a metered dose plunger spray pump coupled with a container containing the composition of any of [1]-[31] above, and instructions for administering the composition using the metered dose plunger spray pump.

[51] A pharmaceutical composition comprising a pharmaceutically acceptable salt of bepotastine and at least one corticosteroid, dibasic sodium phosphate heptahydrate, sodium chloride, edetate disodium, benzalkonium chloride, a blend of microcrystalline cellulose and carboxymethyl cellulose (AVICEL®), and/or polyoxyethylene (20) sorbitan monooleate (polysorbate 80).

[52] A pharmaceutical composition comprising a pharmaceutically acceptable salt of bepotastine and at least one corticosteroid, dibasic sodium phosphate heptahydrate, sodium chloride, edetate disodium, benzalkonium chloride, hydroxypropylmethyl cellulose (HPMC), citric acid monohydrate, and a taste making agent.

[53] The composition of [51] above wherein
the pharmaceutically acceptable salt of bepotastine is besilate and the concentration of bepotastine is 0.5% w/v to 8.00% w/v;
the concentration of corticosteroid is 0.01% w/v to 1% w/v;
the concentration of dibasic sodium phosphate heptahydrate is 0.10% w/v to 1.00% w/v;
the concentration of sodium chloride is 0.9% w/v with 0.5% bepotastine, 0.4% w/v with 2.00%-3.00% bepotastine, 0.3% w/v with 4.00% bepotastine, 0.2% w/v with 6.00% bepotastine, 0.1% w/v with 8.00% bepotastine;
the concentration of edetate disodium is 0.005% w/v to 0.100% w/v;
the concentration of benzalkonium chloride is 0.002% w/v to 0.200% w/v;
the concentration of AVICEL® is 0.5% w/v to 2.5% w/v; and the concentration of polysorbate 80 is 0.005% w/v to 0.050% w/v.

[54] The composition of [52] above wherein
the pharmaceutically acceptable salt of bepotastine is besilate and the concentration of bepotastine is 0.5% w/v to 8.00% w/v;
the concentration of corticosteroid is 0.01% w/v to 1% w/v;
the concentration of dibasic sodium phosphate heptahydrate is 0.10% w/v to 1.00% w/v;
the concentration of sodium chloride is 0.9% w/v with 0.5% bepotastine, 0.4% w/v with 2.00%-3.00% bepotastine, 0.3% w/v with 4.00% bepotastine, 0.2% w/v with 6.00% bepotastine, 0.1% w/v with 8.00% bepotastine;
the concentration of edetate disodium is 0.005% w/v to 0.100% w/v;
the concentration of benzalkonium chloride is 0.002% w/v to 0.200% w/v;

the concentration of HPMC E15 LV is 0.01% w/v to 1.00% w/v, the concentration of citric acid monohydrate is 0.10% w/v to 1.00% w/v, and the concentration of the taste-making agent is 0.01% w/v to 1.00% w/v.

[55] The composition of any of [51] or [53] above wherein the concentration of bepotastine besilate is 4.00% w/v, the concentration of corticosteroid is 0.01% w/v to 1% w/v, the concentration of dibasic sodium phosphate heptahydrate is 0.70% w/v, the concentration of sodium chloride is 0.30% w/v, the concentration of edetate disodium is 0.020% w/v, the concentration of benzalkonium chloride is 0.020% w/v, the concentration of AVICEL® CL-611 is 2.00% w/v, and the concentration of polysorbate 80 is 0.015% w/v.

[56] The composition of any of [52] or [54] above wherein the concentration of bepotastine besilate is 4.00% w/v, the concentration of corticosteroid is 0.01% w/v to 1% w/v, the concentration of dibasic sodium phosphate heptahydrate is 0.70% w/v, the concentration of sodium chloride is 0.30% w/v, the concentration of edetate disodium is 0.020% w/v, the concentration of benzalkonium chloride is 0.020% w/v, the concentration of HPMC E15 LV is 0.10% w/v, the concentration of citric acid monohydrate is 0.10% w/v, and the taste-masking agent is sucralose and the concentration thereof is 0.10% w/v.

[57] The composition of any of [51]-[56] above lacking substantial impurities.

[58] The composition of any of [51]-[57] above optionally containing sorbitol.

[59] The composition of any of [51]-[56] above having pH between pH 4.0 to pH 9.0.

[60] The composition of any of [51]-[56] above having pH between pH 5.0 to pH 6.0.

[61] The composition of any of [51]-[56] above having pH between pH 4.0 to pH 5.5.

[62] A pharmaceutical composition comprising a pharmaceutically acceptable salt of bepotastine and at least one corticosteroid, sodium chloride, edetate disodium, benzalkonium chloride, a blend of microcrystalline cellulose and carboxymethyl cellulose (AVICEL®), and/or polyoxyethylene (20) sorbitan monooleate (polysorbate 80).

[63] The composition of [62] above wherein the corticosteroid is fluticasone propionate and wherein the composition further comprises sodium phosphate dibasic heptahydrate and citric acid monohydrate, wherein the concentration of bepotastine besilate is 3.00% w/v, the concentration of fluticasone propionate is 0.05% w/v, the concentration of dibasic sodium phosphate heptahydrate is 0.70% w/v, the concentration of sodium chloride is 0.60% w/v, the concentration of edetate disodium is 0.020% w/v, the concentration of benzalkonium chloride is 0.0125% w/v, the concentration of citric acid monohydrate is 0.10% w/v, the concentration of AVICEL® is 1.20% w/v, the concentration of polysorbate 80 is 0.01% w/v, and the pH is adjusted to pH 5.0 to pH 7.0 with 2N NaOH.

[64] The composition of [62] above wherein the corticosteroid is budesonide free acid and wherein the composition further comprises sodium phosphate dibasic heptahydrate and citric acid monohydrate, wherein the concentration of bepotastine besilate is 3.00% w/v, the concentration of budesonide is 0.05% w/v, the concentration of dibasic sodium phosphate heptahydrate is 0.70% w/v, the concentration of sodium chloride is 0.60% w/v, the concentration of edetate disodium is 0.020% w/v, the concentration of benzalkonium chloride is 0.0125% w/v, the concentration of citric acid monohydrate is 0.10% w/v, the concentration of AVICEL® is 1.20% w/v, the concentration of polysorbate 80 is 0.01% w/v, and the pH is adjusted to pH 5.0 to pH 6.0 with 2N NaOH.

[65] The composition of [62] above wherein the corticosteroid is mometasone furoate monohydrate and wherein the composition further comprises sodium phosphate dibasic heptahydrate and citric acid monohydrate, wherein the concentration of bepotastine besilate is 3.00% w/v, the concentration of mometasone furoate monohydrate is 0.05% w/v, the concentration of dibasic sodium phosphate heptahydrate is 0.70% w/v, the concentration of sodium chloride is 0.60% w/v, the concentration of edetate disodium is 0.020% w/v, the concentration of benzalkonium chloride is 0.0125% w/v, the concentration of citric acid monohydrate is 0.10% w/v, the concentration of AVICEL® is 1.20% w/v, the concentration of polysorbate 80 is 0.01% w/v, and the pH is adjusted to pH 4.0 to pH 5.5 with 2N NaOH.

[66] The composition of [62] above wherein the corticosteroid is triamcinolone acetonide and wherein the composition further comprises sodium citrate, wherein the concentration of bepotastine besilate is 4.00% w/v, the concentration of triamcinolone acetonide is 0.055% w/v, the concentration of sodium chloride is 0.30% w/v, the concentration of edetate disodium is 0.020% w/v, the concentration of benzalkonium chloride is 0.02% w/v, the concentration of sodium citrate is 0.40% w/v, the concentration of AVICEL® is 2.00% w/v, the concentration of polysorbate 80 is 0.015% w/v, and the pH is adjusted to pH 5.0 to pH 6.0 with 2N NaOH.

[67] The composition of [62] above wherein the corticosteroid is beclomethasone dipropionate and wherein the composition further comprises sodium citrate, wherein the concentration of bepotastine besilate is 4.00% w/v, the concentration of beclomethasone dipropionate is 0.05% w/v, the concentration of sodium chloride is 0.30% w/v, the concentration of edetate disodium is 0.020% w/v, the concentration of benzalkonium chloride is 0.02% w/v, the concentration of sodium citrate is 0.40% w/v, the concentration of AVICEL® is 2.00% w/v, the concentration of polysorbate 80 is 0.015% w/v, and the pH is adjusted to pH 5.0 to pH 6.8 with 2N NaOH.

[68] A pharmaceutical composition comprising at least one corticosteroid as a free form, pharmaceutically acceptable salt, solvate, or physiologically functional derivative thereof, and bepotastine as a free base, pharmaceutically acceptable salt, solvate or physiologically functional derivative thereof, the bepotastine at a concentration from 0.5% w/v to 8.00% w/v inclusive, and a suspending agent interchangeable with a viscosity enhancing agent, the composition formulated as a nasal spray.

The term "pharmaceutically acceptable salt" refers to salts derived from a variety of organic and inorganic counter ions well known in the art and any pharmaceutically acceptable salt soluble in water to form an aqueous solution. The term "effective amount" or "therapeutically effective amount" refers to the amount of an active agent sufficient to induce a desired biological result. That result may be alleviation of the signs, symptoms, or causes of a disease, or any other desired alteration of a biological system. The term "therapeutically effective amount" is used herein to denote any amount of the formulation which causes a substantial improvement in a disease condition when applied to the affected areas repeatedly over a period of time. The amount will vary with the condition being treated, the stage of advancement of the condition, and the type and concentration of formulation applied. Appropriate amounts in any given instance will be readily apparent to those skilled in the art or capable of determination by routine experimentation.

As used herein, "treatment" or "treating," or "palliating" or "ameliorating" are used interchangeably. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. Treatment includes preventing the disease, that is, causing the clinical symptoms of the disease not to develop by administration of a protective composition prior to the induction of the disease; suppressing the disease, that is, causing the clinical symptoms of the disease not to develop by administration of a protective composition after the inductive event but prior to the clinical appearance or reappearance of the disease; inhibiting the disease, that is, arresting the development of clinical symptoms by administration of a protective composition after their initial appearance; preventing re-occurring of the disease and/or relieving the disease, that is, causing the regression of clinical symptoms by administration of a protective composition after their initial appearance.

A "subject," "individual," or "patient," is used interchangeably herein, which refers to a vertebrate, preferably a mammal, more preferably a human. Mammals include, but are not limited to, murines, simians, humans, farm animals, sport animals, and pets. Tissues, cells and their progeny of a biological entity obtained in vitro or cultured in vitro are also encompassed.

The term "free," "free of," "substantially free," or "substantially free of," as used herein, means present in quantities that have less than a material effect on, or confer less than a material advantage to, the pharmaceutical composition or one or more properties of the pharmaceutical composition (e.g., its preservative efficacy). In some embodiments, "free," "free of," "substantially free," or "substantially free of," means not present.

The term "preservative efficacy" or "preservative effectiveness" or "antimicrobial efficacy", as used herein, means that the composition satisfies USP standards as defined in protocol <51> p. 1681, United States Pharmacopeia, 1995: Antimicrobial effectiveness testing; The United States Pharmacopeia, 32nd rev ed., and the National Formulary, 27th ed. Rockville, Md.: USPC; 2009. For example, the preservative is effective in the product examined if (a) the concentrations of viable bacteria are reduced to not more than 0.1% of the initial concentrations by the fourteenth day; (b) the concentrations of viable yeasts and molds remain at or below the initial concentrations during the first 14 days; and (c) the concentration of each test microorganism remains at or below these designated levels during the remainder of the 28-day test period. Similar criteria are defined for BP standards (Efficacy of Antimicrobial Preservation, Appendix XVI C, 1995), and PhEur standards (Efficacy of Antimicrobial Preservation, Chapter VIII. 14, 1992).

Provided herein, inter alia, are novel compositions comprising bepotastine as a free base, a pharmaceutically acceptable salt of bepotastine, e.g., bepotastine besilate, solvate or physiologically functional derivative thereof and a corticosteroid as a free form, pharmaceutically acceptable salt, solvate or physiologically functional derivative thereof. In some embodiments, the compositions are formulated to provide a nasal composition, such as a nasal spray composition. Among other aspects, the composition includes at least a preservative, e.g., about 0.008% w/v benzalkonium chloride, and/or include a viscosity enhancing agent, e.g., a blend of microcrystalline cellulose and carboxymethyl cellulose such as AVICEL®, or a hydroxypropylmethyl cellulose (HPMC, Hypromellose (USAN)) such as HPMC E15 LV. In some embodiments, the compositions further include ethylenediaminetetraacetic acid or a salt thereof (e.g. EDTA or equivalent thereof). Accordingly, the compositions provided herein may have an acceptable shelf-life even after repeated use.

It has now been found that bepotastine as a free base, or a pharmaceutically acceptable salt, solvate or physiologically functional derivative thereof, can advantageously be combined with a corticosteroid as a free form, or a pharmaceutically acceptable salt, solvate or physiologically functional derivative thereof, to provide a stable, very effective combination product or formulation preferably for nasal or ocular treatment. The combination can provide, in a single administration or dosing regime, the antihistaminic properties of bepotastine and the antiinflammatory (and/or other) properties of the steroid, without any significant interference between the two, or adverse reaction in situ.

Thus, in one aspect, the present invention relates to a nasal spray as a combination of bepotastine with a corticosteroid to generally treat symptoms of allergic or non-allergic rhinitis including nasal symptoms resulting from seasonal allergies and environmental irritants. Said nasal spray may be used when the lining of the nose swells and releases fluids which results in what is commonly referred to as "stuffy nose". Also, in another aspect, the product or formulations of the present invention may be used to treat the symptoms of allergic conjunctivitis.

Among the corticosteroids useful for the nasal spray of this invention are, for example, selected from the group consisting of beclomethasone, mometasone, fluticasone, triamcinolone, budesonide, ciclesonide, beclomethasone, dexamethasone, prednisolone, and combinations thereof.

Preferably, the concentration of bepotastine that is incorporated in said nasal spray ranges from 0.5% w/v to 10% w/v, more preferably 2% w/v, 4% w/v, 6% w/v, or 8% w/v.

The corticosteroid concentration ranges from 0.01% w/v to 1% w/v, preferably 0.05% w/v, to thereby provide 10 mcg to 100 mcg, preferably 50 mcg of corticosteroid per spray. The nasal spray may be used to provide up to 8 sprays per day to treat the symptoms of allergic or non-allergic rhinitis.

The nasal spray is preferably utilized as a liquid, but it may also be used in powder form.

Provided herein, inter alia, are novel compositions comprising bepotastine besilate and a corticosteroid. In some embodiments, the compositions are formulated to provide a nasal composition, such as a nasal spray composition. Among other aspects, the compositions may include at least about 0.008% w/v benzalkonium chloride, and/or include hydroxypropylmethyl cellulose E15 LV. In some embodiments, the compositions further include ethylenediaminetetraacetic acid or a salt thereof (e.g. EDTA or equivalent thereof). Accordingly, the compositions provided herein may have an acceptable shelf-life even after repeated use.

Further, additional enhanced properties can be achieved using the compositions (e.g. nasal spray compositions) provided herein. For example, in some embodiments, the compositions provided herein have a substantially uniform droplet size distribution (e.g., a Gaussian size distribution). Moreover, in some embodiments, the novel compositions provided herein have an acceptable taste despite the presence of components, such as bepotastine besilate, having unpleasant tastes.

Unless otherwise stated, all concentrations are in % w/v, and all ranges are inclusive (i.e., the upper and lower values are included within the range).

The first active ingredient for an antihistamine and/or antiallergy effect of the compositions provided herein is (+)-(S)-4-[4-[(4-chlorophenyl)(2-pyridyl)methoxy]piperidino]butyric acid (bepotastine) having the following formula:

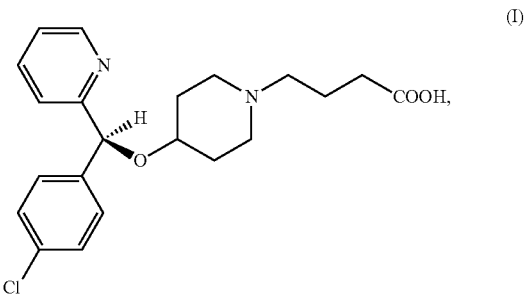 [SMILES: O=C(O)CCCN1CCC(O[C@@H](c2ccc(Cl)cc2)c2ccccn2)CC1]

(I)

including a derivative or a pharmaceutical acceptable salts thereof.

The term "pharmaceutically acceptable salt" refers to salts derived from a variety of organic and inorganic counter ions well known in the art and includes any pharmaceutically acceptable salt soluble in water to form an aqueous solution. They include, by way of example only, basis salts, e.g. alkali metal salts such as sodium, potassium salts, alkaline earth metal salts such as calcium, magnesium, ammonium, tetraalkylammonium salts, and other metal salts such as strontium salts and the like; and acid addition salts, e.g., inorganic acid addition salts such as hydrochloride, hydrobromide, and organic acid addition salts such as besilate, benzoate, toluenesulfonate, tartrate, mesylate, acetate, maleate, oxalate and the like; salts with hydrohalic acid such as hydrochloride, hydrobromide and the like; salts with inorganic acid such as sulfate, nitrate, phosphate and the like; salts with organic acid such as acetate, propionate, hydroxyacetate, 2-hydroxypropionate, pyruvate, malonate, succinate, maleate, fumarate, dihydroxyfumarate, oxalate, benzoate, cinnamate, salicylate, methanesulfonate, ethanesulfonate, benzenesulfonate, p-toluenesulfonate, cyclohexylsulfamate, 4-aminosalicylate and the like. The above-mentioned compound to be used in the compositions provided herein is generally preferably an acid addition salt, and of these acid addition salts, benzenesulfonate (besilate) and benzoate are more preferable. In some embodiments, the active ingredient of the compositions provided herein is bepotastine besilate of the formula:

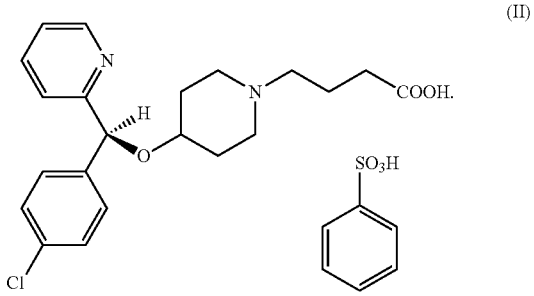 [SMILES: O=C(O)CCCN1CCC(O[C@@H](c2ccc(Cl)cc2)c2ccccn2)CC1 ; O=S(=O)(O)c1ccccc1]

(II)

In some embodiments, the concentration of (+)-(S)-4-[4-[(4-chlorophenyl)(2-pyridyl)methoxy]piperidino] butyric acid, a pharmaceutically acceptable salt, solvate, or physiologically functional derivative thereof (e.g., bepotastine besilate) in the composition, calculated on the basis of molecular weight of the besilate salt form of bepotastine, is from about 0.5% w/v to about 10% w/v (e.g., about 0.5% w/v, about 1% w/v, about 2% w/v, about 3% w/v, about 4% w/v, about 5% w/v, about 6% w/v, about 7% w/v, about 8% w/v, about 9% w/v, or about 10% w/v). In some embodiments, the compositions provided herein have a concentration of bepotastine besilate from about 5% w/v to about 10% w/v. In some embodiments, the compositions provided herein have a concentration of bepotastine besilate from about 10% w/v to about 20% w/v (e.g., about 10% w/v, about 11% w/v, about 12% w/v, about 13% w/v, about 14% w/v, about 15% w/v, about 16% w/v, about 17% w/v, about 18% w/v, about 19% w/v, or about 20% w/v). In some embodiments, the compositions provided herein have more than 20% w/v bepotastine besilate.

(+)-(S)-4-[4-[(4-Chlorophenyl)(2-pyridyl)methoxy]piperidino]butyric acid or a pharmaceutically acceptable salt thereof can be produced by, for example, the methods described in PCT Patent Publication Nos. WO98/29409, WO2008/123701, WO2009/075504 and the like.

The second active ingredient is a corticosteroid which is useful for suppressing inflammatory conditions, e.g. nasal inflammatory conditions. The corticosteroid may be a free form or may be a pharmaceutically acceptable salt, solvate, or physiologically functional derivative thereof. The pharmaceutically acceptable salts of corticosteroid include sodium salt. The solvate includes a hydrate. The physiologically functional derivatives include esters with a lower alkanoic acid (e.g., acetic acid, propionic acid), furancarboxylic acid and the like; acetonide. Preferable examples include beclomethasone, beclomethasone dipropionate, mometasone furoate monohydrate, fluticasone propionate, fluticasone furoate, triamcinolone, triamcinolone acetonide, budesonide, ciclesonide, beclomethasone sodium, dexamethasone sodium, prednisolone acetate, and mixtures thereof.

In some embodiments, the concentration of a corticosteroid free form, a pharmaceutically acceptable salt, solvate, or physiologically functional derivative thereof in the composition, calculated on the basis of molecular weight of the respective anhydrous salt form of corticosteroid, is from about 0.01% w/v to about 1% w/v.

The compositions provided herein may include an effective amount of an antimicrobial preservative. Preservatives can be used to inhibit microbial growth (e.g., bacterial or yeast) in the compositions. An "effective amount" of a preservative is that amount necessary to prevent the growth of microorganisms in the composition. In some embodiments, the concentration or amount of preservative is generally that which is necessary to prevent microbial growth in the composition for a storage period of at least six months. In certain embodiments, the concentration or amount of preservative is that which is necessary to satisfy USP standards as defined in protocol <51> p. 1681, United States Pharmacopeia, 1995, Antimicrobial effectiveness testing; The United States Pharmacopeia, 32nd rev ed., and the National Formulary, 27th ed. Rockville, Md.: USPC; 2009.

Examples of pharmaceutically acceptable preservatives include benzethonium chloride, butylparaben, methyl paraben, ethyl paraben, propyl paraben, benzalkonium chloride, cetyl pyridinium chloride, thimerosal, chlorobutanol, phenylethyl alcohol, benzyl alcohol, potassium sorbate, sodium benzoate, sorbic acid, oxychloro complexes (otherwise known as PURITE®), phenylmercuric acetate, chlorobutanol, benzyl alcohol, parabens, and thimerosal or combinations thereof. In some embodiments, the preservative is benzalkonium chloride (BAK). In some embodiments, the compositions include a preservative in combination with a chelating agent, as set forth below.

In one embodiment, the antimicrobial preservative (e.g. benzalkonium chloride) may be present in the composition in an amount of from about 0.002% w/v to about 0.200% w/v. In another embodiment, the antimicrobial preservative (e.g. benzalkonium chloride) may be present in the composition in an amount of from about 0.005% w/v to about 0.100% w/v. In yet another embodiment, the antimicrobial preservative (e.g. benzalkonium chloride) may be present in the composition in an amount of from about 0.010% w/v to about 0.050% w/v.

In some embodiments, the preservative in the composition is benzalkonium chloride. In some embodiments, benzalkonium chloride may be present in the composition in an amount of from about 0.008% w/v to about 0.015% w/v. In some embodiments, the compositions provided herein have a concentration of benzalkonium chloride from about 0.008% w/v to about 0.010% w/v, from about 0.010% w/v to about 0.012% w/v, from about 0.012% w/v to about 0.015% w/v, or more than 0.015% w/v. In some embodiments, the compositions provided herein have about 0.008% w/v, about 0.009% w/v, about 0.010% w/v, about 0.0011% w/v, about 0.012% w/v, about 0.013% w/v, about 0.014% w/v, or about 0.015% w/v benzalkonium chloride. In some embodiments, the compositions provided herein include only a single preservative. In some embodiments, the compositions provided herein include only two preservatives.

The compositions provided herein can include an effective amount of a chelating agent. The term "chelating agent" refers to a compound or mixture of compounds used in a formulation that is capable of complexing a metal, as understood by those of ordinary skill in the chemical art. Chelating agents complex metal ions such as iron, copper and lead, and may act as antioxidant synergist as otherwise these heavy metals catalyze oxidation reactions. Presently preferred chelating agents non-exclusively include different salts of edetic acid. These nonexclusively include edetate disodium, edetate calcium disodium, edetate tetrasodium, edetate trisodium, and combinations thereof. In one embodiment, the chelating agent may be present in the composition in an amount of from about 0.005% w/v to about 0.100% w/v. In another embodiment, the chelating agent may be present in the composition in an amount of from about 0.010% w/v to about 0.050% w/v. In yet another embodiment, the chelating agent may be present in the composition in an amount of from about 0.010% w/v to about 0.020% w/v.

In some embodiments, the chelating agent in the composition is ethylenediaminetetraacetic acid or a salt thereof. In some embodiments, benzalkonium chloride may be present in the composition in an amount of from about 0.002% w/v to about 0.200% w/v. In some embodiments, the compositions provided herein have a concentration of ethylenediaminetetraacetic acid or a salt thereof from about 0.002% w/v to about 0.010% w/v, from about 0.010% w/v to about 0.050% w/v, from about 0.050% w/v to about 0.200% w/v, or more than 0.200% w/v. In some embodiments, the compositions provided herein have about 0.005% w/v, about 0.010% w/v, about 0.020% w/v, about 0.030% w/v, or about 0.040% w/v ethylenediaminetetraacetic acid or a salt thereof. In some embodiments, the compositions provided herein include only a chelating agent.

The compositions provided herein can include an effective amount of a viscosity agent. The term "viscosity agent," or "viscosity enhancing agent", as used herein, refers to molecular species in the compositions provided herein that increase the viscosity of the composition. Preferred viscosity enhancing agents include, e.g., polyols, polymers, sugars, and polysaccharides. In some embodiments, the viscosity agent has a viscosity of 2% solution in water of about 12-18 mPA·s (USP/EP/JP)

It will be appreciated by one skilled in the art that viscosity agents may also be suspending agents, and that suspending agents may also be viscosity agents.

In some embodiments, the viscosity agent in the composition is hydroxypropylmethyl cellulose E15 LV (HPMC E15 LV) (a water-soluble cellulose ether having a methoxyl content of about 28-30%, a hydroxypropoxyl content of about 7-12%, and a viscosity of 2% solution in water of about 12-18 mPA·s (USP/EP/JP), available from Dow as METHOCEL®). In some embodiments, HPMC E15 LV may be present in the composition in an amount of from about 0.01% w/v to about 1.00% w/v. In some embodiments, the compositions provided herein have a concentration of HPMC E15 LV from about 0.01% w/v to about 0.05% w/v, from about 0.05% w/v to about 0.10% w/v, from about 0.10% w/v to about 0.50% w/v, from about 0.50% w/v to about 1.00% w/v, or more than 1.00% w/v. In some embodiments, the compositions provided herein have about 0.02% w/v, about 0.05% w/v, about 0.10% w/v, about 0.20% w/v, or about 0.30% w/v HPMC E15 LV. In some embodiments, the compositions provided herein include only a single viscosity agent.

In some embodiments, the viscosity agent in the composition facilitates more or less uniform dispersement of the active ingredient in a liquid, that is, it is a suspending agent. Such an agent provides for increased or optimized residence time of the active ingredient in nasal tissue and minimized agent ingredient outside nasal tissue (e.g., in the throat), while beneficially providing thixotropic properties that still permit expression of the composition from a spray or other administration orifice. Examples of such suspending agents include a blend of microcrystalline cellulose and carboxymethyl cellulose, e.g., AVICEL® (FMC), e.g., AVICEL® CL-611, AVICEL® RC-581, AVICEL® RC-591, and other pharmaceutically acceptable thixotropic agents. AVICEL® CL-611 and AVICEL® RC-591 are examples of strong suspending agents. According to the manufacturer, AVICEL® CL-611 is similar to AVICEL® RC-591. AVICEL® CL-611 is more compatible with a higher concentration of salts in solution, while the viscosity and suspension properties of AVICEL® RC-591 are more sensitive to the amount of salts in solution. AVICEL® CL-611 also imparts a physical property of viscosity, so is considered as both a suspending agent and a viscosity enhancing agent. In one embodiment, the concentration of AVICEL® CL-611 is from 0.5% w/v to 2.5% w/v. In one embodiment, the concentration of AVICEL® CL-611 is 2.00% w/v. Another example of a suspending agent is a polyoxyethylene (20) sorbitan monooleate (polysorbate 80), e.g., at 0.005% w/v to 0.050% w/v; in one embodiment at 0.015% w/v.

In one embodiment in formulating a disclosed composition, AVICEL® was dissolved in about 75% of the water with high speed mixing for about five minutes. Polysorbate 80 was mixed with a small portion of the water and was added to the AVICEL® solution and mixed at high speed for about five minutes. Sodium phosphate was added to the resulting mixture with mixing, followed by a tonicity agent (e.g., sodium chloride), a chelating agent (e.g., EDTA) and bepotastine besilate and corticosteroid. The pH was adjusted with NaOH. A preservative (e.g., benzalkonium chloride) was added last, followed by the addition of water to 100%.

The compositions provided herein may optionally include an effective amount of a taste masking agent. In some embodiments, formulations of bepotastine in the presence of a corticosteroid do not contain a taste-masking agent. The taste-masking agent is one or more agents or compounds which, optionally together, successfully mask or cover the (potential) unpleasant taste of one or more components of the compositions provided herein when present in an effective amount. In some embodiments, the compositions comprise two or more taste masking agents, such as a polyol sweetener and a high intensity sweetener. In some embodiments, the compositions include only a single taste masking agent in the absence of any other sweeteners, flavorants or taste masking agents.

In some embodiments, the taste masking agent is (tri) sodium citrate, sodium citrate, sodium chloride, sodium bicarbonate, and combinations thereof.

In some embodiments, the taste masking agent is a polyol sweetener. A specific example of one category of polyol sweeteners include sugars, in particular a sugar selected from the group consisting of dextrose, sucrose, maltose, fructose, lactose, and combinations thereof. Another specific example of another category of polyol sweeteners include sugar alcohols, in particular sugar alcohols selected from the group consisting of xylitol, sorbitol, mannitol, maltitol, isomaltol, isomalt, erythritol, lactitol, maltodextrin, hydrogenated starch hydrolysates, D-xylose, trehalose, and combinations thereof.

In some embodiments, the taste masking agent is a high intensity sweetener or a flavor. Useful high intensity sweeteners may be selected from the group consisting of sucralose, neotame, aspartame, salts of acesulfame in particular the potassium salt of acesulfame (acesulfame K), alitame, saccharin and its salts, cyclamic acid and its salts, glycyrrhizin, dihydrochalcones e.g. NHDC, thaumatin, monellin, stevioside, Twinsweet (aspartame-acesulfame salt) and combinations thereof. Still other examples of suitable taste masking agents include salts of gluconate, such as sodium gluconate.

In some embodiments, the taste-masking agent is one or more flavoring agents, optionally in combination with one or more food acids. Flavors which can be used in the compositions according to the present invention include, but are not limited to, coconut, coffee, cola, chocolate, vanilla, orange, lemon, grape fruit, menthol, licorice, anise, apricot, caramel, honey, pineapple, strawberry, raspberry, tropical fruits, cherries, cinnamon, peppermint, wintergreen, spearmint, eucalyptus and mint flavors. In one embodiment, the flavors are chosen from menthol, caramel, coffee, cola, and combinations thereof, in particular the combination of menthol and caramel.

In some embodiments, the taste-masking agent in the compositions is sucralose (e.g. in the absence of other sweeteners, flavorants or taste masking agents). In some embodiments, sucralose may be present in the composition in an amount of from about 0.01% w/v to about 1.00% w/v. In some embodiments, the compositions provided herein have a concentration of sucralose from about 0.01% w/v to about 0.05% w/v, from about 0.05% w/v to about 0.10% w/v, from about 0.10% w/v to about 0.50% w/v, from about 0.50% w/v to about 1.00% w/v, or more than 1.00% w/v. In some embodiments, the compositions provided herein have about 0.02% w/v, about 0.05% w/v, about 0.10% w/v, about 0.20% w/v, or about 0.30% w/v of sucralose.

The compositions provided herein can further include other ingredients and components such as a tonicity agent or a buffer. The term "tonicity agent," as used herein, denotes pharmaceutically acceptable tonicity agents. Tonicity agents are used to modulate the tonicity of the formulation. The formulation can be hypotonic, isotonic or hypertonic. Isotonicity in general relates to the osmotic pressure of a solution usually relative to that of human blood serum. The formulation according to the invention can be hypotonic, isotonic or hypertonic but will preferably be isotonic. An isotonic formulation is liquid or liquid reconstituted from a solid form, e.g. from a lyophilised form and denotes a solution having the same tonicity as some other solution with which it is compared, such as physiologic salt solution and the blood serum. Suitable tonicity agents comprise but are not limited to metal chloride (e.g., sodium chloride, potassium chloride), glycerine and any component from the group of amino acids, sugars, in particular glucose. Tonicity agents are generally used in an amount of about 5 mM to about 500 mM. In a preferred formulation the amount of tonicity agent is in the range of about 50 mM to about 300 mM. In some embodiments, the compositions provided herein include only a tonicity agent (e.g. sodium chloride).

In some embodiments, the tonicity agent in the composition is sodium chloride. In some embodiments, sodium chloride may be present in the composition in an amount of from about 0.10% w/v to about 1.00% w/v. In some embodiments, the compositions provided herein have a concentration of sodium chloride from about 0.10% w/v to about 0.20% w/v, from about 0.20% w/v to about 0.50% w/v, from about 0.50% w/v to about 0.75% w/v, from about 0.75% w/v to about 1.00% w/v, or more than 1.00% w/v. In some embodiments, the compositions provided herein have about 0.20% w/v, about 0.30% w/v, about 0.40% w/v, about 0.50% w/v, or about 0.70% w/v sodium chloride.

The term "buffer" as used herein denotes a pharmaceutically acceptable excipient, which stabilizes the pH of a pharmaceutical preparation. Preferred pharmaceutically acceptable buffers comprise but are not limited to borate-buffers, histidine-buffers, citrate-buffers, succinate-buffers, acetate-buffers, tartrate-buffers, and phosphate-buffers. The abovementioned buffers are generally used in an amount of about 1 mM to about 100 mM, preferably of about 5 mM to about 50 mM and more preferably of about 10 mM-20 mM.

In some embodiments, the buffer in the composition is citric acid (e.g. citric acid monohydrate) and/or sodium phosphate (e.g. sodium phosphate dibasic heptahydrate). In some embodiments, the citric acid and/or sodium phosphate buffers may be present in the composition in an amount of from about 0.10% w/v to about 1.00% w/v. In some embodiments, the compositions provided herein have a concentration of citric acid or sodium phosphate from about 0.10% w/v to about 0.20% w/v, from about 0.20% w/v to about 0.50% w/v, from about 0.50% w/v to about 0.75% w/v, from about 0.75% w/v to about 1.00% w/v, or more than 1.00% w/v. In some embodiments, the compositions provided herein have about 0.20% w/v, about 0.30% w/v, about 0.40% w/v, about 0.50% w/v, or about 0.70% w/v citric acid or sodium phosphate.

The pH can be adjusted at a value of from about 4.0 to about 9.0 and preferably about 5.0 to about 8.0 and still preferably about 6.0 to about 7.0 with an acid or a base as known in the art, e.g. hydrochloric acid, acetic acid, phosphoric acid, sulfuric acid and citric acid, sodium hydroxide and potassium hydroxide. The pH of the compositions provided herein is adjusted to not less than about 4.0, 5.0, or 6.0, and not more than about 8.5, 8.0, or 9.0. In some embodiments, the compositions provided herein include only a buffer. In other embodiments, the compositions provided herein include only two buffers.

The compositions provided herein may include a solvent. In some embodiments, the solvent is water. In some embodiments, the compositions provided herein include only a single solvent (e.g. water). In the compositions provided herein, other similar or non-similar efficacious ingredients may be added appropriately in a manner avoiding impairment of the object of the present invention.

Provided herein are compositions (e.g. nasal compositions such as nasal spray compositions) including (+)-(S)-4-[4-[(4-chlorophenyl)(2-pyridyl)methoxy]piperidino]butyric acid as a free base, pharmaceutical acceptable salt, solvate, or physiologically functional derivative thereof, and a corticosteroid as a free form, pharmaceutically acceptable salt, solvate, or physiologically functional derivative thereof, in combination with a preservative, optionally a chelating agent, optionally a viscosity agent, optionally a taste masking agent, and optionally a tonicity agent and a buffer, as described above. In some embodiments, the invention relates to a composition comprising bepotastine besilate and a corticosteroid.

In some embodiments, the composition comprises bepotastine besilate and a corticosteroid, and may further include a preservative, e.g., benzalkonium chloride. In some embodiments, the composition includes at least about 0.008% w/v benzalkonium chloride. In some embodiments, the composition includes at least about 0.010% w/v benzalkonium chloride. In some embodiments, the composition includes at least about 0.0125% w/v benzalkonium chloride. The composition may further include a chelating agent, such as ethylenediaminetetraacetic acid or a salt thereof. In some embodiments, the composition includes from about 0.002% w/v to about 0.200% w/v ethylenediaminetetraacetic acid or a salt thereof. In some embodiments, the composition includes about 0.02% w/v ethylenediaminetetraacetic acid or a salt thereof. The composition may further include a viscosity agent, e.g., hydroxypropylmethyl cellulose E15 LV. In some embodiments, the composition includes from about 0.01% w/v to about 1.00% w/v hydroxypropylmethyl cellulose E15 LV. In some embodiments, the composition includes about 0.10% w/v hydroxypropylmethyl cellulose E15 LV. The composition may further include a taste masking agent, e.g., sucralose. In some embodiments, the composition includes from about 0.01% w/v to about 1.00% w/v sucralose. In some embodiments, the composition includes about 0.10% w/v sucralose. In some embodiments, the concentration of bepotastine besilate is from about 0.5% w/v to about 10% w/v. In some embodiments, the concentration of bepotastine besilate is about 2% w/v. In some embodiments, the concentration of bepotastine besilate is about 4% w/v. In some embodiments, the concentration of bepotastine besilate is about 6% w/v. In some embodiments, the concentration of bepotastine besilate is about 8% w/v.

In some embodiments, the nasal composition includes bepotastine besilate and a corticosteroid, and at least about 0.008% w/v benzalkonium chloride. In some embodiments, the composition includes at least about 0.008% w/v benzalkonium chloride. In some embodiments, the composition includes at least about 0.010% w/v benzalkonium chloride. In some embodiments, the composition includes at least about 0.0125% w/v benzalkonium chloride. The composition may further include a chelating agent, such as ethylenediaminetetraacetic acid or a salt thereof. In some embodiments, the composition includes from about 0.002% w/v to about 0.200% w/v ethylenediaminetetraacetic acid or a salt thereof. In some embodiments, the composition includes about 0.02% w/v ethylenediaminetetraacetic acid or a salt thereof. The composition may further include a viscosity agent, e.g., hydroxypropylmethyl cellulose E15 LV. In some embodiments, the composition includes from about 0.01% w/v to about 1.00% w/v hydroxypropylmethyl cellulose E15 LV. In some embodiments, the composition includes about 0.10% w/v hydroxypropylmethyl cellulose E15 LV. The composition may further include a taste masking agent, e.g., sucralose. In some embodiments, the composition includes from about 0.01% w/v to about 1.00% w/v sucralose. In some embodiments, the composition includes about 0.10% w/v sucralose. In some embodiments, the concentration of bepotastine besilate is from about 0.5% w/v to about 10% w/v. In some embodiments, the concentration of bepotastine besilate is about 2% w/v. In some embodiments, the concentration of bepotastine besilate is about 4% w/v. In some embodiments, the concentration of bepotastine besilate is about 6% w/v. In some embodiments, the concentration of bepotastine besilate is about 8% w/v.

In some embodiments, the nasal composition includes bepotastine besilate and a corticosteroid and hydroxypropylmethyl cellulose E15 LV. In some embodiments, the composition includes from about 0.01% w/v to about 1.00% w/v hydroxypropylmethyl cellulose E15 LV. In some embodiments, the composition includes about 0.10% w/v hydroxypropylmethyl cellulose E15 LV. The composition may further include a preservative, e.g., benzalkonium chloride. In some embodiments, the composition includes at least about 0.008% w/v benzalkonium chloride. In some embodiments, the composition includes at least about 0.010% w/v benzalkonium chloride. In some embodiments, the composition includes at least about 0.0125% w/v benzalkonium chloride. The composition may further include a chelating agent, such as ethylenediaminetetraacetic acid or a salt thereof. In some embodiments, the composition includes from about 0.002% w/v to about 0.200% w/v ethylenediaminetetraacetic acid or a salt thereof. In some embodiments, the composition includes about 0.02% w/v ethylenediaminetetraacetic acid or a salt thereof. The composition may further include a taste masking agent, e.g., sucralose. In some embodiments, the composition includes from about 0.01% w/v to about 1.00% w/v sucralose. In some embodiments, the composition includes about 0.10% w/v sucralose. In some embodiments, the concentration of bepotastine besilate is from about 0.5% w/v to about 10% w/v. In some embodiments, the concentration of bepotastine besilate is about 2% w/v. In some embodiments, the concentration of bepotastine besilate is about 4% w/v. In some embodiments, the concentration of bepotastine besilate is about 6% w/v. In some embodiments, the concentration of bepotastine besilate is about 8% w/v.

In some embodiments, the nasal composition includes bepotastine besilate and a corticosteroid, at least about 0.008% w/v benzalkonium chloride, and hydroxypropylmethyl cellulose E15 LV. In some embodiments, the composition further includes ethylenediaminetetraacetic acid or a salt thereof. In some embodiments, the composition further includes a taste masking agent, e.g., sucralose. In some embodiments, the concentration of bepotastine besilate is from about 0.5% to about 10% w/v. In some embodiments, the concentration of bepotastine besilate is about 2% w/v. In some embodiments, the concentration of bepotastine besilate is about 4% w/v. In some embodiments, the concentration of bepotastine besilate is about 6% w/v. In some embodiments, the concentration of bepotastine besilate is about 8% w/v.

In some embodiments, the nasal composition includes about 0.0125% w/v benzalkonium chloride, about 0.1% w/v hydroxypropylmethyl cellulose E15 LV, about 0.1% sucralose, about 0.02% w/v ethylenediaminetetraacetic acid or a salt thereof. In some embodiments, the concentration of bepotastine besilate is from about 0.5% w/v to about 10% w/v. In some embodiments, the concentration of bepotastine besilate is about 2% w/v. In some embodiments, the concentration of bepotastine besilate is about 4% w/v. In some embodiments, the concentration of bepotastine besilate is about 6% w/v. In some embodiments, the concentration of bepotastine besilate is about 8% w/v.

In some embodiments, the nasal composition contains only bepotastine besilate and a corticosteroid, citric acid, sodium phosphate, metal chloride, sucralose, hydroxypropylmethyl cellulose, ethylenediaminetetraacetic acid or a salt thereof, about 0.008% w/v to about 0.015% w/v benzalkonium chloride, sodium hydroxide and water. In some embodiments, the metal chloride is sodium chloride. In some embodiments, the hydroxypropylmethyl cellulose is hydroxypropylmethyl cellulose E15 LV. In some embodiments, the nasal composition consists of bepotastine besilate, citric acid, sodium phosphate, metal chloride, sucralose, hydroxypropylmethyl cellulose, ethylenediaminetetraacetic acid or a salt thereof, about 0.0125% w/v to about 0.015% w/v benzalkonium chloride, sodium hydroxide and water. In some embodiments, the concentration of bepotastine besilate is from about 0.5% w/v to about 10% w/v. In some embodiments, the concentration of bepotastine besilate is about 2% w/v. In some embodiments, the concentration of bepotastine besilate is about 4% w/v. In some embodiments, the concentration of bepotastine besilate is about 6% w/v. In some embodiments, the concentration of bepotastine besilate is about 8% w/v.

A person having ordinary skill in the art will recognize that, in some embodiments, components of the compositions detailed above, except the active ingredients, namely, bepotastine and corticosteroid, may be removed or replaced in keeping with known practices in the art of pharmaceutical formulations.

Provided herein are methods of treating rhinitis, mucosal inflammation associated with rhinitis, sinusitis, and/or symptoms associated thereto. Nasal symptoms include symptoms known to be problematic for patients with rhinitis or sinusitis: nasal itching, rhinorrhea (runny nose), nasal congestion (stuffy nose), and sneezing. As used herein, the term "rhinitis" refers to inflammation of the nasal mucous membranes resulting from, e.g., a cold, flu, or allergies. Rhinitis may be characterized by one or more cold-like symptoms including, for example, rhinorrhea, sneezing, nasal congestion, and increased nasal secretion. Rhinitis can include acute rhinitis, chronic rhinitis, allergic rhinitis, seasonal allergic rhinitis, perennial allergic rhinitis, vasomotor rhinitis, infectious rhinitis, and atrophic rhinitis. As used herein, the term "sinusitis" refers to inflammation of the paranasal sinuses, which can be the result of infection (e.g., bacterial, fungal or viral), allergic or autoimmune causes. It should be appreciated that newer classifications of sinusitis may refer to the condition as "rhinosinusitis" since inflammation of the sinuses typically does not occur without some inflammation of the nose as well.

According to the present invention, rhinitis may generally include any inflammation of the nasal mucous membrane. Symptoms of rhinitis can generally include one or more cold-like symptoms including, for example, rhinorrhea, increased nasal secretion, nasal congestion, sneezing and catarrh. Rhinitis can also include both allergic rhinitis and non-allergic rhinitis. "Allergic rhinitis" refers to any allergic reaction of the nasal mucosa and may include hay fever (seasonal allergic rhinitis) and perennial rhinitis (non-seasonal allergic rhinitis). "Non-allergic rhinitis" refers to eosinophilic non-allergic rhinitis which is found in subjects with negative skin tests and those who have numerous eosinophils in their nasal secretions. In some embodiments, the compositions provided herein are useful in treating allergic rhinitis.

Sinusitis can include a condition that is similar to rhinitis generally characterized by inflammation of the paranasal sinuses. Sinusitis can be acute (i.e., less than four weeks), subacute (i.e., 4-12 weeks) or chronic (i.e., for 12 weeks or more), and can include such symptoms as headache, upper jaw and teeth pain, swelling of the eyelids and ocular tissue, and superficial pain associated with tactile compression of the nose.

For nasal administration of the nasal compositions, various devices are available in the art for the generation of drops, droplets and sprays. For example, the nasal spray composition can be administrated into the nasal passages of a subject by means of a dropper (or pipet) that includes a glass, plastic or metal dispensing tube. Fine droplets and sprays can be provided by an intranasal pump dispenser or squeeze bottle as well known in the art.

Other means for delivering the nasal compositions, such as inhalation via a metered dose inhaler (MDI), may also be used according to the present invention. Several types of MDIs are regularly used for administration by inhalation. These types of devices can include breath-actuated MDI, dry powder inhaler (DPI), spacer/holding chambers in combination with MDI, and nebulizers. The term "MDI" as used herein refers to an inhalation delivery system comprising, for example, a canister containing an active agent dissolved or suspended in a propellant optionally with one or more excipients, a metered dose valve, an actuator, and a mouthpiece. The canister is usually filled with a solution or suspension of an active agent, such as the nasal spray composition, and a propellant, such as one or more hydrofluoroalkanes. When the actuator is depressed a metered dose of the solution is aerosolized for inhalation. Particles comprising the active agent(s) are propelled toward the mouthpiece where they may then be inhaled by a subject.

Either aqueous or "wet" spray formulations, or pressurized, non-aqueous aerosol "dry" spray formulations propelled by hydrofluoroalkane may be used, either of which may contain a built-in dose counter.

In one embodiment, the delivery system is a metered dose plunger spray pump. The pump and actuator are commercially available (Aptar (Valois)) (pump: VP7A/100 CS-20-AG 908EVAE2 EM24, 100 µL spray, 20 mm crimp, 24 mm dip tube length; polypropylene (PP) body, 11R51 or 12R10 stainless steel spring, ethylene vinyl acetate (EVA) gasket, aluminum ferrule) (actuator: CB18 NAC/3/B Bepaule+CAP B25A, polypropylene body). In one embodiment, the pump is coupled to a neck of a container containing the pharmaceutical bepotastine besilate composition. Coupling methods include, but are not limited to, a crimp-seal to the container, a torqued coupling onto matching threads of the container, depression of a snap-cap pump into place with the container, etc. The above delivery system may be physically modified, e.g., to accommodate specific bottles for a nasal spray composition, etc. In one embodiment, a kit contains the pump, container, and instructions for use to treat a patient with the disclosed bepotastine besilate composition.

After appropriately packaging the nasal spray composition in a squeeze bottle, for example, the nasal composition may be intranasally administered to one or both nasal cavities of the subject at a desired dosage. For example, the plastic dispensing tube may be appropriately placed in one nostril of the subject. The squeeze bottle may then be squeezed so that the nasal spray composition is aerosolized into a fine droplet mist and spread across the nasal mucosa of the subject. The dosage frequency of the nasal spray composition may vary depending upon personal or medical needs of the subject. Generally, dosage frequencies may range from about once per day, per nostril to about four times daily. A typical dose may contain, for example, two sprays per nostril BID.

The following examples illustrate certain specific embodiments of the invention and are not meant to limit the scope of the invention.

Example 1

Components, Formulation, Manufacture of Bepotastine Besilate/Corticosteroid Nasal Spray Using Fluticasone Propionate As A Non-Limiting Exemplary Corticosteroid Bepotastine besilate is a white to off-white, odorless, crystalline powder. The bepotastine drug substance physiological mode of action is inhibition of histamine $H_1$ receptors to relieve typical symptoms associated with allergic rhinitis. The water content, solubility, particle size distribution and hydration state of the bepotastine drug substance have no impact on the performance or manufacturability of the bepotastine besilate nasal spray suspensions. The bepotastine drug substance is a non-hygroscopic white crystalline powder that dissolves readily in the nasal spray formulation vehicle.

Fluticasone propionate is a white to off-white, crystalline synthetic trifluorinated corticosteroid used to treat inflammatory symptoms related to asthma and allergic rhinitis. For the drug products, fluticasone propionate is practically insoluble in water and remains in a suitably sized particle form in the aqueous suspension.

The following table lists the excipients found in the clinical formulations (including placebo), as well as the applicable compendial grade and primary function for each of the excipient components for each of the nasal spray drug products. All excipient components listed are compendial; there are no new excipient raw materials.

Excipients for Bepotastine Besilate/Fluticasone Propionate Nasal Sprays

| Excipients | Primary Function |
|---|---|
| AVICEL ® CL-611 (microcrystalline cellulose and carboxymethyl cellulose sodium), NF | Suspending Agent/Viscosity Enhancing Agent |
| Polysorbate 80, NF | Suspending Agent |
| Dibasic Sodium Phosphate Heptahydrate, USP | Buffer |
| Sodium Chloride, USP | Tonicity Agent |
| Edetate Disodium, USP | Chelating Agent |
| Benzalkonium Chloride, NF/USP | Preservative |
| 2N Sodium Hydroxide, NF | pH Adjuster |
| 1N Hydrochloric Acid, NF | pH Adjuster |
| Purified Water, USP | Solvent |

For the vehicle formulation, the phosphate buffer was chosen because of its good buffer capacity at the target pH of 6.4, as well as compatibility with the drug substances.

Sodium chloride was added primarily as a tonicity agent to maintain the osmolality of the product at 275-400 mOsm/kg. The AVICEL® CL-611 (microcrystalline cellulose with carboxymethyl cellulose) and polysorbate 80 were added as agents to maintain the fluticasone propionate particles suspended in the aqueous matrix. The EDTA in the formulation was added as a chelating agent.

The preservative, benzalkonium chloride (BAK), at a concentration of 0.200 mg/mL, was selected because of its long history as a preservative in other nasal formulations. BAK has also been shown to be compatible with the bepotastine drug substance in previous ophthalmic stability studies. The BAK at this concentration has been demonstrated to be an effective preservative.

In one embodiment, the bepotastine/fluticasone nasal spray drug products were delivered in a suspension form through a nasal spray pump.

The bepotastine besilate drug substance has been previously formulated and marketed as an ophthalmic solution for ocular itching by ISTA Pharmaceuticals, Inc. in the U.S. under the BEPREVE® brand name.

Fluticasone propionate has been previously formulated for the treatment of symptoms associated with allergic rhinitis in commercial nasal spray suspension forms (e.g., FLONASE®, GlaxoSmithKline). The fluticasone active ingredient is insoluble in water, as such it would necessitate it to be in a suspension form for administration through a nasal spray pump. The use of microcrystalline cellulose and carboxymethyl cellulose (AVICEL® CL 611) maintained the fluticasone particles evenly distributed within the suspension matrix. The solid fluticasone particles were milled to an appropriately small particle size to further optimize the pharmaceutical action of fluticasone propionate.

In one embodiment, the bepotastine/fluticasone nasal sprays were administered topically to the nasal passages via a metered dose spray pump. The solubilized bepotastine in aqueous solution and/or the fluticasone propionate in suspension comes in contact with the nasal mucosa, where both can subsequently penetrate into the surrounding tissues and vessels and elicit a pharmaceutical effect.

The pH of the bepotastine/fluticasone nasal spray suspensions were optimized to a target pH of 6.4 with the phosphate buffer. The target pH in phosphate buffer maintained the chemical stability of both bepotastine besilate and fluticasone propionate. The pH was within the range of the maximum octanol-water partition coefficient, which is predicted to give the optimal conditions for the molecule to penetrate through cell membranes.

To ensure manufacture of a homogeneous suspension, AVICEL® CL-611 was dispersed in solution prior to the addition of the other components. This was accomplished by first mixing approximately 80% of the total purified water for the batch with AVICEL® using a high shear mixer or homogenizer. AVICEL® contains both soluble (carboxymethyl cellulose) and insoluble (microcrystalline cellulose) components that interact with each other and water to form a stable suspension matrix. AVICEL® was added before any other components so as to not compromise the stability and rheological properties of the suspension matrix.

After AVICEL® dispersion, the fluticasone was dispersed as a slurry into the AVICEL® and mixed with the high shear mixer or homogenizer. The salt excipients were then added while mixing continuously to ensure full dissolution of ingredients. Bepotastine besilate was then added to the solution and the pH was adjusted with sodium hydroxide or hydrochloric acid. Following pH adjustment, benzalkonium chloride was added and a final pH step was performed to ensure the pH was 6.4. Purified water was added to the final q.s. weight.

Selection of the manufacturing process was a function of the requirements and characteristics of the formulation and the dosage form, specifically that the product was a non-sterile aqueous suspension, which in one embodiment is dosed with a standard metered dose nasal spray pump.

Example 2

Composition of Placebo and Active Concentrations of Bepotastine Besilate Nasal Spray

| Ingredient | Function | Placebo (% w/v) | 2.0% (% w/v) | 4.0% (% w/v) | 6.0% (% w/v) |
|---|---|---|---|---|---|
| Bepotastine Besilate | Active | — | 2.00 | 4.00 | 6.00 |
| Corticosteroid | Anti-inflammatory | — | 0.05 | 0.05 | 0.05 |
| Citric Acid, USP | Buffer | 0.10 | 0.10 | 0.10 | 0.10 |
| Sodium Phosphate Dibasic Buffer Heptahydrate, USP | Buffer | 0.70 | 0.70 | 0.70 | 0.70 |
| Sodium Chloride, USP | Tonicity Agent | 0.65 | 0.35 | 0.20 | 0.10 |
| Sucralose, USP | Taste Masking Agent | 0.10 | 0.10 | 0.10 | 0.10 |
| Sorbitol, USP | Taste Masking Agent | 0.35 | 0.35 | 0.35 | 0.35 |
| Hydroxypropylmethyl Cellulose (E4M), USP | Viscosity Agent | 0.10 | 0.10 | 0.10 | 0.10 |
| Benzalkonium Chloride, NF/USP | Preservative | 0.005 | 0.005 | 0.005 | 0.005 |
| 2N Sodium Hydroxide, NF | pH Adjuster | pH adjustment to 6.8 | | | |
| Purified Water | Solvent | q.s. to 100% of volume | | | |

The compositions in the table above (Example 2) failed to pass the USP 51 Preservative Efficacy Test.

Example 3

Composition of Placebo and Active Concentrations of Bepotastine Besilate Nasal Spray

| Component and Qualify Standard (and Grade, if applicable) | Function | Placebo (% w/v) | 2% (% w/v) | 4% (% w/v) | 6% (% w/v) |
|---|---|---|---|---|---|
| Bepotastine Besilate | Active | — | 2.00 | 4.00 | 6.00 |
| Corticosteroid | Anti-inflammatory | — | 0.05 | 0.05 | 0.05 |
| Citric Acid Monohydrate, USP | Buffer | 0.10 | 0.10 | 0.10 | 0.10 |
| Dibasic Sodium Phosphate Heptahydrate, USP | Buffer | 0.70 | 0.70 | 0.70 | 0.70 |
| Sodium Chloride, USP | Tonicity Agent | 0.70 | 0.40 | 0.30 | 0.20 |
| Sucralose, NF | Taste Masking Agent | 0.10 | 0.10 | 0.10 | 0.10 |
| Hydroxypropyl-methyl Cellulose (E4M), USP | Viscosity Agent | 0.10 | 0.10 | 0.10 | 0.10 |
| Edetate Disodium, USP | Chelating Agent | 0.02 | 0.02 | 0.02 | 0.02 |
| Benzalkonium Chloride NF/USP | Preservative | 0.0125 | 0.0125 | 0.0125 | 0.0125 |
| 2N Sodium Hydroxide, NF | pH Adjuster | pH adjustment to 6.8 | | | |
| Purified Water, USP | Solvent | q.s. to 100% of volume | | | |

The compositions in the table above (Example 3) successfully passed the USP 51 Preservative Efficacy Test; without being held to a specific theory, this was likely due to the increased concentration of benzalkonium chloride in Example 3 (from 0.005% BAK in formulation 1 versus 0.0125% in Example 3) and/or the presence of EDTA in this formulation.

Example 4

Taste Making Agents

A laboratory study was performed to identify ingredients that could empirically mask the bitter taste of the bepotastine besilate active ingredient. A surrogate bitterness model was used to evaluate the ability of each or a combination of the ingredients to mask the bitter taste (data not shown). For these experiments, caffeine was used as the surrogate bitter agent and mixed with formulation ingredients such as sorbitol and sucralose; salt; citrate and phosphate buffers; and orange, tangerine, and lemon flavoring agents. Based on the taste results of the formulation matrix, sucralose and sorbitol had the largest impact on bitterness as compared to the other ingredients.

Bepotastine and a corticosteroid may be formulated as a suspension. AVICEL® CL-611, RC-591 are strong suspending agents/viscosity enhancing agents and may be added whether the active is soluble and thus does not require a suspension (e.g., bepotastine without a corticosteroid) or is less soluble and thus does require a suspension (e.g., bepotastine with a corticosteroid, e.g., fluticasone). The suspensions were thixotropic, and immediately liquefied upon even slight movement, as in removal for use. According to the manufacturer (FMC), AVICEL® CL-611 is similar to AVICEL® RC-591. AVICEL® CL-611 is more compatible with a higher concentration of salts in solution, while the viscosity and suspension properties of AVICEL® RC-591 are more sensitive to the amount of salts in solution. AVICEL® CL-611 also imparts a physical property of viscosity, so is considered as both a suspending agent and a viscosity enhancing agent.

Example 5

Compositions Including Bepotastine Besilate and a Corticosteroid Concentrations of Ingredients of Nasal Spray Including Fluticasone Propionate

| Component | % w/v |
|---|---|
| AVICEL ® RC-591 | 1.20% |
| Fluticasone propionate | 0.05% |
| Polysorbate 80 | 0.01% |
| Citric Acid Monohydrate | 0.10% |
| Sodium Phosphate Dibasic Heptahydrate | 0.70% |
| Bepotastine Besilate | 3.00% |
| Sodium Chloride | 0.60% |
| EDTA | 0.02% |
| BAK | 0.0125% |
| 2N NaOH | pH 5.0 to 7.0 |

Concentrations of Ingredients of Nasal Spray Including Budesonide

| Component | % w/v |
|---|---|
| AVICEL ® RC-591 | 1.20% |
| Budesonide Free Acid | 0.05% |
| Polysorbate 80 | 0.01% |
| Citric Acid Monohydrate | 0.10% |
| Sodium Phosphate Dibasic Heptahydrate | 0.70% |
| Bepotastine Besilate | 3.00% |
| Sodium Chloride | 0.60% |
| EDTA | 0.02% |
| BAK | 0.0125% |
| 2N NaOH | pH 5.0 to 6.0 |

Concentrations of Ingredients of Nasal Spray Including Mometasone

| Component | % w/v |
|---|---|
| AVICEL ® RC-591 | 1.20% |
| Mometasone Furoate Monohydrate | 0.05% |
| Polysorbate 80 | 0.01% |
| Citric Acid Monohydrate | 0.10% |
| Sodium Phosphate Dibasic Heptahydrate | 0.70% |
| Bepotastine Besilate | 3.00% |
| Sodium Chloride | 0.60% |
| EDTA | 0.02% |
| BAK | 0.0125% |
| 2N NaOH | pH 4.0 to 5.5 |

Concentrations of Ingredients of Nasal Spray Including Triamcinolone

| Component | % w/v |
|---|---|
| AVICEL ® CL-611 | 2.00% |
| Triamcinolone Acetonide | 0.055% |
| Polysorbate 80 | 0.015% |

-continued

| Component | % w/v |
|---|---|
| Sodium Citrate | 0.40% |
| Bepotastine Besilate | 4.00% |
| Sodium Chloride | 0.30% |
| EDTA | 0.02% |
| Benzalkonium Chloride | 0.02% |
| 2N NaOH | pH 5.0 to 6.0 |

Concentrations of Ingredients of Nasal Spray Including Beclomethasone

| Component | % w/v |
|---|---|
| AVICEL ® CL-611 | 2.00% |
| Beclomethasone Dipropionate | 0.05% |
| Polysorbate 80 | 0.015% |
| Sodium Citrate | 0.40% |
| Bepotastine Besilate | 4.00% |
| Sodium Chloride | 0.30% |
| EDTA | 0.02% |
| Benzalkonium Chloride | 0.02% |
| 2N NaOH | pH 5.0 to 6.8 |

Polysorbate 80 and AVICEL® RC-591, CL-611 may be used as suspending agents without adding any viscosity agent and are used to maintain fluticasone and other steroids in suspension.

Using bepotastine/fluticasone formulation development as a non-limiting example only, formulation was as follows. The pH of the bepotastine/fluticasone nasal spray suspensions were optimized to a target pH of 6.4 with the phosphate buffer. The target pH in phosphate buffer was important in maintaining the chemical stability of both bepotastine and fluticasone. The pH was also important for bepotastine since this pH is within the range of the maximum octanol-water partition coefficient, which is predicted to give the best conditions for the molecule to penetrate through cell membranes.

Chemical stability studies were performed to determine if the formulation would likely achieve a commercially practical shelf-life. Studies were performed at 25° C. and 40° C. in moisture impermeable amber glass bottles. The 4-month stability results at elevated temperature demonstrated that the formulation would likely be stable at room temperature for a commercially practical shelf life period (data shown below):

Combination Placebo Stability Results 25° C./40% RH

| Storage Condition: 25° C. ± 5° C., 40% ± 5% RH (Upright) Product Size: 15 mL | | Bottle: Amber glass Pump: N/A (Crimped butyl stopper) | |
|---|---|---|---|
| Item | Initial | 2 Months | 4 Months |
| Description: Product Appearance (White to straw colored suspension) | Pass Pass | Pass Pass | Pass Pass |
| Bepotastine Besilate Identification (Presence of bepotastine peak) | Negative Negative | NA | NA |
| Bepotastine Besilate Assay (90-110% of Label Amount) | NA | NA | NA |
| Ethyl Ester Impurity (Not More Than 1.0%) | NA | NA | NA |
| Any Other Individual Impurity (Not More Than 0.5%) | NA | NA | NA |
| Bepotastine Total Impurities (Not More Than 2.0%) | NA | NA | NA |
| Bepotastine Optical Isomer (% of Active) (Not More Than 1.0%) | NA | NA | NA |
| Fluticasone Propionate Identification (RRT = 0.95-1.05 is a positive indicator) | Negative Negative | NA | NA |
| Fluticasone Propionate Assay (90-115% of Label Amount) | NA | NA | NA |
| Fluticasone Related Any Individual Impurity (Report) | NA | NA | NA |
| Fluticasone Related Total Impurities (Report) | NA | NA | NA |
| Benzalkonium Chloride (BAK) Assay (80-125% of Theoretical Amount) | 96 98 | 98 97 | 96 97 |
| pH (6.3-7.3) | 6.4 6.4 | 6.4 6.4 | 6.4 6.4 |
| Osmolality (Report) | 359 359 | 363 367 | 367 365 |
| EDTA (80-120% of Theoretical Amount) | 101 104 | 100 101 | 99 99 |

NA = Not Applicable

Combination Placebo Stability Results 40° C./20% RH

| Storage Condition: 40° C. ± 5° C., 20% RH ± 5% (Upright) Product Size: 15 mL | | Bottle: Amber glass Pump: N/A (Crimped butyl stopper) | |
|---|---|---|---|
| Item | Initial | 2 Months | 4 Months |
| Description: Product Appearance (White to straw colored suspension) | Pass Pass | Pass Pass | Pass Pass |
| Bepotastine Besilate Identification (Presence of bepotastine peak) | Negative Negative | NA | NA |
| Bepotastine Besilate Assay (90-110% of Label Amount) | NA | NA | NA |
| Ethyl Ester Impurity (Not More Than 1.0%) | NA | NA | NA |
| Any Other Individual Impurity (Not More Than 0.5%) | NA | NA | NA |
| Bepotastine Total Impurities (Not More Than 2.0%) | NA | NA | NA |
| Bepotastine Optical Isomer (% of Active) (Not More Than 1.0%) | NA | NA | NA |
| Fluticasone Propionate Identification (RRT = 0.95-1.05 is a positive indicator) | Negative Negative | NA | NA |
| Fluticasone Propionate Assay (90-115% of Label Amount) | NA | NA | NA |
| Fluticasone Related Any Individual Impurity (Report) | NA | NA | NA |
| Fluticasone Related Total Impurities (Report) | NA | NA | NA |
| Benzalkonium Chloride (BAK) | 96 | 97 | 96 |

| Item | (Initial) | (2 Months) | (4 Months) |
|---|---|---|---|
| Assay | 98 | 96 | 97 |
| (80-125% of Theoretical Amount) | | | |
| pH | 6.4 | 6.4 | 6.4 |
| (6.3-7.3) | 6.4 | 6.4 | 6.4 |
| Osmolality | 359 | 364 | 363 |
| (Report) | 359 | 362 | 371 |
| EDTA | 101 | 99 | 97 |
| (80-120% of Theoretical Amount) | 104 | 100 | 98 |

NA = Not Applicable

Fluticasone/Bepotastine Combination Stability Results 25° C./40% RH

| Storage Condition: 25° C. ± 5° C., 40% RH ± 5% (Upright) Product Size: 15 mL | Bottle: Amber glass (SGD, France) Pump: Aptar VP7A/100 µL |
|---|---|

| Item | Initial | 2 Months | 4 Months |
|---|---|---|---|
| Description: Product Appearance (White to straw colored suspension) | Pass Pass | Pass Pass | Pass Pass |
| Bepotastine Besilate Identification (Presence of bepotastine peak) | Positive Positive | NA NA | NA NA |
| Bepotastine Besilate Assay (90-110% of Label Amount) | 102 102 | 102 101 | 100 98 |
| Ethyl Ester Impurity (Not More Than 1.0%) | 0.5 0.4 | 0.2 0.2 | 0.1 0.1 |
| Any Other Individual Impurity (Not More Than 0.5%) | ND ND | ND ND | ND ND |
| Bepotastine Total Impurities (Not More Than 2.0%) | 0.5 0.4 | 0.2 0.2 | 0.1 0.1 |
| Bepotastine Optical Isomer (% of Active) (Not More Than 1.0%) | 0.1 0.1 | 0.1 0.1 | 0.1 0.1 |
| Fluticasone Propionate Identification (RRT = 0.95-1.05 is a positive indicator) | Positive Positive | NA NA | NA NA |
| Fluticasone Propionate Assay (90-115% of Label Amount) | 101 100 | 99 99 | 101 102 |
| Fluticasone Related Any Individual Impurity (Report) | ND ND | <LOQ ND | 0.1 (Compound E) ND |
| Fluticasone Related Total Impurities (Report) | ND ND | <LOQ ND | 0.1 ND |
| Benzalkonium Chloride (BAK) Assay (80-125% of Theoretical Amount) | 99 100 | 99 100 | 100 98 |
| pH (6.3-7.3) | 6.4 6.4 | 6.4 6.4 | 6.4 6.4 |
| Osmolality (Report) | 347 348 | 349 347 | 352 348 |
| EDTA (80-120% of Theoretical Amount) | 101 104 | 101 102 | 98 98 |

NA = Not Applicable; ND = Not Detected; LOQ = Limit of Quantitation (0.08%)

Fluticasone/Bepotastine Stability Results 40° C./20% RH

| Storage Condition: 40° C. ± 5° C., 20% RH ± 5% (Upright) Product Size: 15 mL | Bottle: Amber glass (SGD, France) Pump: Aptar VP7A/100 µL |
|---|---|

| Item | Initial | 2 Months | 4 Months |
|---|---|---|---|
| Description: Product Appearance (White to straw colored suspension) | Pass Pass | Pass Pass | Pass Pass |
| Bepotastine Besilate Identification (Presence of bepotastine peak) | Positive Positive | NA NA | NA NA |
| Bepotastine Besilate Assay (90-110% of Label Amount) | 102 102 | 101 99 | 104 100 |
| Ethyl Ester Impurity (Not More Than 1.0%) | 0.5 0.4 | ND ND | ND ND |
| Any Other Individual Impurity (Not More Than 0.5%) | ND ND | ND ND | ND ND |
| Bepotastine Total Impurities (Not More Than 2.0%) | 0.5 0.4 | ND ND | ND ND |
| Bepotastine Optical Isomer (% of Active) (Not More Than 1.0%) | 0.1 0.1 | 0.2 0.2 | 0.3 0.3 |
| Fluticasone Propionate Identification (RRT = 0.95-1.05 is a positive indicator) | Positive Positive | NA NA | NA NA |
| Fluticasone Propionate Assay (90-115% of Label Amount) | 101 100 | 100 99 | 102 102 |
| Fluticasone Related Any Individual Impurity (Report) | ND ND | ND ND | 0.1, 0.1 (Unknown RRT = 0.37) 0.1, (Unknown RRT = 0.39) |
| Fluticasone Related Total Impurities (Report) | ND ND | ND ND | 0.2 0.1 |
| Benzalkonium Chloride (BAK) Assay (80-125% of Theoretical Amount) | 99 100 | 99 100 | 101 100 |
| pH (6.3-7.3) | 6.4 6.4 | 6.4 6.4 | 6.4 6.4 |
| Osmolality (Report) | 347 348 | 359 351 | 348 350 |
| EDTA (80-120% of Theoretical Amount) | 101 104 | 98 98 | 94 92 |

NA = Not Applicable; ND = Not Detected

The formulations are as follows. Formulation 1 and placebo, with concentration ranges and for a specific embodiment, respectively, are presented in the following two tables:

Formulation 1 and placebo (concentration ranges)

| Ingredient | Function | Active (% w/v) | Placebo (% w/v) |
|---|---|---|---|
| Bepotastine Besilate | Active | 0.5-8.00 | — |
| Fluticasone Propionate | Anti-inflammatory | 0.01-1.00 | — |
| Hydroxypropylmethyl Cellulose (E15LV) | Viscosity Agent | 0.01-1.00 | 0.01-1.00 |
| Polysorbate 80 | Suspending Agent | 0.005-0.050 | 0.005-0.050 |
| Citric Acid Monohydrate | Buffer | 0.10-1.00 | 0.10-1.00 |
| Sodium Phosphate Dibasic Heptahydrate | Buffer | 0.10-1.00 | 0.10-1.00 |
| Sodium chloride | Tonicity Agent | 0.9 with 0.5% active 0.4 with 2.00%-3.00% active 0.3 with 4.00% active 0.2 with 6.00% active 0.1 with 8.00% active | 0.70 |
| Sucralose | Taste Masking Agent | 0.01-1.00 | 0.01-1.00 |
| EDTA, USP | Chelating Agent | 0.005-0.100 | 0.005-0.100 |
| Benzalkonium Chloride, NF/USP | Preservative | 0.002-0.200 | 0.002-0.200 |
| 2N NaOH | pH Adjuster | pH to 4.0-9.0 | pH 4.0-9.0 |
| Purified Water | Solvent | q.s. to 100% of volume | q.s. to 100% of volume |

Formulation 1 and placebo (specific concentrations)

| Ingredient | Function | Active (% w/v) | Placebo (% w/v) |
|---|---|---|---|
| Bepotastine Besilate | Active | 4.00 | — |
| Fluticasone Propionate | Anti-inflammatory | 0.05 | — |
| Hydroxypropylmethyl Cellulose (E15LV) | Viscosity Agent | 0.10 | 0.10 |
| Polysorbate 80 | Suspending Agent | 0.01 | 0.01 |
| Citric Acid Monohydrate | Buffer | 0.10 | 0.10 |
| Sodium Phosphate Dibasic Heptahydrate | Buffer | 0.70 | 0.70 |
| Sodium chloride | Tonicity Agent | 0.30 | 0.70 |
| Sucralose | Taste Making Agent | 0.10 | 0.10 |
| EDTA, USP | Chelating Agent | 0.02 | 0.02 |
| Benzalkonium Chloride, NF/USP | Preservative | 0.0125 | 0.0125 |
| 2N NaOH | pH Adjuster | pH to 6.8 | PH 6.8 |
| Purified Water | solvent | q.s. to 100% of volume | q.s. to 100% of volume |

Formulation 2 and placebo, with concentration ranges and for a specific embodiment, respectively, are presented in the following two tables:

Formulation 2 and placebo (ranges)

| Ingredient | Function | Active (% w/v) | Placebo (% w/v) |
|---|---|---|---|
| Bepotastine Besilate | Active | 0.5-8.00 | — |
| Fluticasone Propionate | Anti-inflammatory | 0.01-1.00 | — |
| AVICEL ® CL-611, RC-581, or RC-591 (blend of microcrystalline cellulose and carboxymethyl cellulose sodium), NF | Suspending Agent/ Viscosity Enhancing Agent | 0.5-2.5 | 0.5-2.5 |
| Polysorbate 80, NF | Suspending Agent | 0.005-0.050 | 0.005-0.050 |
| Dibasic Sodium Phosphate Heptahydrate, USP | Buffer | 0.10-1.00 | 0.10-1.00 |
| Sodium Chloride, USP | Tonicity Agent | 0.9 with 0.5% active 0.4 with 2.00%-3.00% active 0.3 with 4.00% active 0.2 with 6.00% active 0.1 with 8.00% active | 0.80 |
| Edetate Disodium, USP | Chelating Agent | 0.005-0.100 | 0.005-0.100 |
| Benzalkonium Chloride, NF/USP | Preservative | 0.002-0.200 | 0.002-0.200 |
| 2N Sodium Hydroxide, NF | pH Adjuster | pH adjustment to 4.0-9.0 | pH adjustment to 4.0-9.0 |
| Purified Water, USP | Solvent | q.s. to 100% | q.s. to 100% |

Formulation 2 and placebo (specific)

| Ingredient | Function | Active (% w/v) | Placebo (% w/v) |
|---|---|---|---|
| Bepotastine Besilate | Active | 4.00 | — |
| Fluticasone Propionate | Anti-inflammatory | 0.05 | — |
| AVICEL ® CL-611 (blend of microcrystalline cellulose and carboxymethyl cellulose sodium), NF | Suspending Agent/ Viscosity Enhancing Agent | 2.00 | 2.00 |
| Polysorbate 80, NF | Suspending Agent | 0.015 | 0.015 |
| Dibasic Sodium Phosphate Heptahydrate, USP | Buffer | 0.70 | 0.70 |
| Sodium Chloride, USP | Tonicity Agent | 0.30 | 0.80 |
| Edetate Disodium, USP | Chelating Agent | 0.02 | 0.02 |
| Benzalkonium Chloride, NF/USP | Preservative | 0.020 | 0.020 |

| Ingredient | Function | Active (% w/v) | Placebo (% w/v) |
| --- | --- | --- | --- |
| 2N Sodium Hydroxide, NF | pH Adjuster | pH adjustment to 6.4 | pH adjustment to 6.4 |
| Purified Water, USP | Solvent | q.s. to 100% | q.s. to 100% |

Formulation 3 and placebo (specific)

| Ingredient | Function | Active (% w/v) | Placebo (% w/v) |
| --- | --- | --- | --- |
| Bepotastine Besilate | Active | 3.00 | — |
| Fluticasone Propionate | Anti-inflammatory | 0.05 | — |
| AVICEL ® RC-591 | Suspending Agent/ Viscosity Enhancing Agent | 1.20 | 1.20 |
| Polysorbate 80, NF | Suspending Agent | 0.01 | 0.01 |
| Citric Acid Monohydrate | Buffer | 0.10 | 0.10 |
| Dibasic Sodium Phosphate Heptahydrate, USP | Buffer | 0.70 | 0.70 |
| Sodium Chloride, USP | Tonicity Agent | 0.60 | 0.70 |
| Edetate Disodium, USP | Chelating Agent | 0.02 | 0.02 |
| Benzalkonium Chloride, NF/USP | Preservative | 0.0125 | 0.0125 |
| 2N Sodium Hydroxide, NF | pH Adjuster | pH adjustment to 5-7 | pH adjustment to 5-7 |
| Purified Water, USP | Solvent | q.s. to 100% | q.s. to 100% |

Formulation 4 and placebo (specific)

| Ingredient | Function | Active (% w/v) | Placebo (% w/v) |
| --- | --- | --- | --- |
| Bepotastine Besilate | Active | 3.00 | — |
| Budesonide Free Acid | Anti-inflammatory | 0.05 | — |
| AVICEL ® RC-591 | Suspending Agent/ Viscosity Enhancing Agent | 1.20 | 1.20 |
| Polysorbate 80, NF | Suspending Agent | 0.01 | 0.01 |
| Citric Acid Monohydrate | Buffer | 0.10 | 0.10 |
| Dibasic Sodium Phosphate Heptahydrate, USP | Buffer | 0.70 | 0.70 |
| Sodium Chloride, USP | Tonicity Agent | 0.60 | 0.70 |
| Edetate Disodium, USP | Chelating Agent | 0.02 | 0.02 |
| Benzalkonium Chloride, NF/USP | Preservative | 0.0125 | 0.0125 |
| 2N Sodium Hydroxide, NF | pH Adjuster | pH adjustment to 5.0-6.0 | pH adjustment to 5.0-6.0 |
| Purified Water, USP | Solvent | q.s. to 100% | q.s. to 100% |

Formulation 5 and placebo (specific)

| Ingredient | Function | Active (% w/v) | Placebo (% w/v) |
| --- | --- | --- | --- |
| Bepotastine Besilate | Active | 3.00 | — |
| Mometasone Furoate Monohydrate | Anti-inflammatory | 0.05 | — |
| AVICEL ® RC-591 | Suspending Agent/ Viscosity Enhancing Agent | 1.20 | 1.20 |
| Polysorbate 80, NF | Suspending Agent | 0.01 | 0.01 |
| Citric Acid Monohydrate | Buffer | 0.10 | 0.10 |
| Dibasic Sodium Phosphate Heptahydrate, USP | Buffer | 0.70 | 0.70 |
| Sodium Chloride, USP | Tonicity Agent | 0.60 | 0.70 |
| Edetate Disodium, USP | Chelating Agent | 0.02 | 0.02 |
| Benzalkonium Chloride, NF/USP | Preservative | 0.0125 | 0.0125 |
| 2N Sodium Hydroxide, NF | pH Adjuster | pH adjustment to 4.0-5.5 | pH adjustment to 4.0-5.5 |
| Purified Water, USP | Solvent | q.s. to 100% | q.s. to 100% |

The associated antimicrobial preservative effectiveness test data for each of Formulation 1 and Formulation 2, the 12 month stability data at both 25° C. and 40° C. for Formulation 1, and the 4 month stability data at both 25° C. and 40° C. for Formulation 2, were determined to provide satisfactory preservative efficacy, and be stable during a commercially practical shelf life period (data shown below).

The preservative utilized in all of the bepotastine/fluticasone nasal spray formulations was benzalkonium chloride, which historically has had a long history as an effective preservative in topical preparations including ophthalmic drops and nasal sprays. The compatibility of benzalkonium chloride and bepotastine has been previously confirmed (data not shown). Benzalkonium chloride and fluticasone have also been shown to be compatible in the commercial preparations of fluticasone propionate suspension, such as FLONASE®. To determine the antimicrobial effectiveness of the BAK in each of the different nasal spray formulations, a study was performed for antimicrobial preservative effectiveness testing per USP <51>.

The drug products met the USP <51> criteria for Category 2 drug products. The verification (neutralization qualification) for the antimicrobial preservative effectiveness testing was also performed.

Log₁₀ Reduction Results for Placebo Formulation

| | LOG REDUCTION | | | |
|---|---|---|---|---|
| Organism | 0 HOUR | 7 DAY | 14 DAY | 28 DAY |
| *Aspergillus brasiliensis (niger)* | 0.07 | ~4.15 | ~4.27 | >4.27 |
| *Candida albicans* | 0.77 | >4.45 | >4.45 | >4.45 |
| *Escherichia coli* | >4.11 | >4.11 | >4.11 | >4.11 |
| *Staphylococcus aureus* | >4.46 | >4.46 | >4.46 | >4.46 |
| *Pseudomonas aeruginosa* | ~4.23 | >4.23 | >4.23 | >4.23 |

Log₁₀ Reduction Results for Bepotastine/Fluticasone Combination Formulation

| | LOG REDUCTION | | | |
|---|---|---|---|---|
| Organism | 0 HOUR | 7 DAY | 14 DAY | 28 DAY |
| *Aspergillus brasiliensis (niger)* | 0.06 | 0.24 | 0.62 | 1.22 |
| *Candida albicans* | −0.04 | 1.19 | 2.55 | ~4.02 |
| *Escherichia coli* | >4.11 | >4.11 | >4.11 | >4.11 |
| *Staphylococcus aureus* | 1.31 | >4.46 | >4.46 | >4.46 |
| *Pseudomonas aeruginosa* | >4.23 | >4.23 | >4.23 | >4.23 |

Log₁₀ Reduction Results for Fluticasone Propionate Formulation

| | LOG REDUCTION | | | |
|---|---|---|---|---|
| Organism | 0 HOUR | 7 DAY | 14 DAY | 28 DAY |
| *Aspergillus brasiliensis (niger)* | 0.18 | >4.27 | >4.27 | >4.27 |
| *Candida albicans* | 1.49 | >4.45 | >4.45 | >4.45 |
| *Escherichia coli* | >4.11 | >4.11 | >4.11 | >4.11 |
| *Staphylococcus aureus* | >4.46 | >4.46 | >4.46 | >4.46 |
| *Pseudomonas aeruginosa* | >4.23 | >4.23 | >4.23 | >4.23 |

Log₁₀ Reduction Results for Bepotastine Besilate Formulation

| | LOG REDUCTION | | | |
|---|---|---|---|---|
| Organism | 0 HOUR | 7 DAY | 14 DAY | 28 DAY |
| *Aspergillus brasiliensis (niger)* | 0.17 | 0.26 | 0.66 | 1.03 |
| *Candida albicans* | 0.00 | 0.93 | 2.43 | ~4.08 |
| *Escherichia coli* | >4.11 | >4.11 | >4.11 | >4.11 |
| *Staphylococcus aureus* | >0.73 | >4.46 | >4.46 | >4.46 |
| *Pseudomonas aeruginosa* | >4.23 | >4.23 | >4.23 | >4.23 |

Bepotastine was monitored for impurities during stability evaluation. The only impurity found was the ethyl ester precursor of bepotastine from bepotastine synthesis. Upon solvation and aging in the formulation, the ethyl ester group on the bepotastine molecule is hydrolyzed to form the bepotastine drug. The results are shown below:

Formulation 2 stored at 40° C. (percent of formulated amount)

| | Bepotastine Besilate | Fluticasone Propionate |
|---|---|---|
| Initial | 102%, 102% | 101%, 100% |
| 2 months | 101%, 99% | 100%, 99% |
| 4 months | 104%, 100% | 102%, 102% |

Formulation 2 stored at 25° C. (percent of formulated amount)

| | Bepotastine Besilate | Fluticasone Propionate |
|---|---|---|
| Initial | 102%, 102% | 101%, 100% |
| 2 months | 102%, 101% | 99%, 99% |
| 4 months | 100%, 98% | 101%, 102% |

AVICEL® CL-611 at a concentration of 2.00% was used for all subsequent evaluations in both bepotastine (with besilate salt) combined with corticosteroid formulations.

The formulations and the associated AET data and stability data were determined to provide satisfactory preservative efficacy and stability during a commercially practical shelf life period.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating at least one of rhinitis, mucosal inflammation associated with rhinitis, sinusitis, rhinosinusitis, and runny nose and stuffy nose symptoms associated with rhinitis, mucosal inflammation associated with rhinitis, sinusitis, or rhinosinusitis in a patient in need of such treatment, the method comprising:
    nasally administering a pharmaceutical composition, the composition consisting essentially of:
    a corticosteroid, the corticosteroid formulated with a sufficient concentration of a suspending agent excipient to result in a corticosteroid suspension, the corticosteroid as a free form, pharmaceutically acceptable salt, or solvate;
    bepotastine as a free base, pharmaceutically acceptable salt, or solvate at a concentration ranging from 0.5% w/v to 8.00% w/v in aqueous solution;
    at least one pharmaceutically compatible buffer;
    at least one tonicity agent;
    at least one chelating agent; and one of either
    a blend of microcrystalline cellulose and carboxymethyl cellulose with polyoxyethylene (20) sorbitan monooleate (polysorbate 80) or hydroxypropylmethylcellulose (HPMC) E15 LV with citric acid monohydrate and a taste-masking agent;
    the composition administered to the patient in need thereof in a dose regimen effective to treat at least one of rhinitis, mucosal inflammation associated with rhinitis, sinusitis, rhinosinusitis, and runny nose and stuffy nose symptoms associated with rhinitis, mucosal inflammation associated with rhinitis, sinusitis, or rhinosinusitis.

2. The method of claim 1 wherein bepotastine in the composition administered is at a concentration ranging from 2.00% w/v to 4.00% w/v and corticosteroid in the composition administered is at a concentration ranging from 0.01% w/v to 1% w/v.

3. The method of claim 1 wherein administration is from 1 time a day to 4 times a day.

4. The method of claim 1 wherein bepotastine in the composition administered is at a concentration of either 3.00% w/v or 4.00% w/v and administration is 1 time a day or at more than 12 hour intervals.

5. The method of claim 3 wherein the dose regimen is effective to treat allergic rhinitis.

6. The method of claim 1 wherein the composition administered consists essentially of:
the corticosteroid;
the bepotastine;
dibasic sodium phosphate heptahydrate at a concentration of 0.10% w/v to 1.00% w/v;
sodium chloride at a concentration of 0.9% w/v with 0.5% bepotastine, 0.4% w/v with 2.00%-3.00% bepotastine, 0.3% w/v with 4.00% bepotastine, 0.2% w/v with 6.00% bepotastine, 0.1% w/v with 8.00% bepotastine;
edetate disodium at a concentration of 0.005% w/v to 0.100% w/v;
benzalkonium chloride at a concentration of 0.002% w/v to 0.200% w/v; and one of either:
the blend of microcrystalline cellulose and carboxymethyl cellulose at a concentration of 0.5% w/v to 2.5% w/v and polyoxyethylene (20) sorbitan monooleate (polysorbate 80) at a concentration of 0.005% w/v to 0.050% w/v, or
the hydroxypropylmethylcellulose (HPMC) E15 LV at a concentration of 0.01% w/v to 1.00% w/v, the citric acid monohydrate at a concentration of 0.10% w/v to 1.00% w/v, and the taste-masking agent at a concentration of 0.01% w/v to 1.00% w/v.

7. The method of claim 1 wherein the composition administered consists essentially of:
the corticosteroid;
the bepotastine;
dibasic sodium phosphate heptahydrate at a concentration of 0.70% w/v,
sodium chloride at a concentration of 0.30% w/v,
edetate disodium at a concentration of 0.020% w/v,
benzalkonium chloride at a concentration of 0.020% w/v, and one of either:
the blend of microcrystalline cellulose and carboxymethyl cellulose at a concentration of 2.00% w/v and polysorbate 80 at a concentration of 0.015% w/v, or
the HPMC E15 LV at a concentration of 0.10% w/v, the citric acid monohydrate at a concentration of 0.10% w/v, and sucralose at a concentration of 0.10% w/v.

8. The method of claim 1 wherein the pharmaceutically acceptable salt of bepotastine is besilate.

9. The method of claim 1 wherein the corticosteroid is selected from the group consisting of beclomethasone, beclomethasone dipropionate, mometasone furoate monohydrate, fluticasone propionate, fluticasone furoate, triamcinolone, triamcinolone acetonide, budesonide, budesonide free acid, ciclesonide, beclomethasone sodium, dexamethasone sodium, prednisolone acetate, and mixtures thereof.

10. A method to treat at least one of rhinitis, mucosal inflammation associated with rhinitis, sinusitis, rhinosinusitis, and runny nose and stuffy nose symptoms associated with rhinitis, mucosal inflammation associated with rhinitis, sinusitis, or rhinosinusitis, the method comprising:
nasally administering to a patient in need thereof a composition consisting essentially of:
bepotastine besilate;
a corticosteroid, the corticosteroid formulated with a sufficient concentration of a suspending agent excipient to result in a corticosteroid suspension, the corticosteroid as a free form, pharmaceutically acceptable salt, solvate, or physiologically functional derivative thereof;
dibasic sodium phosphate heptahydrate;
sodium chloride, edetate disodium;
benzalkonium chloride; and one of either:
a blend of microcrystalline cellulose and carboxymethyl cellulose and/or polyoxyethylene (20) sorbitan monooleate (polysorbate 80), or
hydroxypropylmethyl cellulose (HPMC), citric acid monohydrate, and
taste-masking agent;
under conditions to treat at least one of rhinitis, mucosal inflammation associated with rhinitis, sinusitis, rhinosinusitis, and runny nose and stuffy nose symptoms associated with rhinitis, mucosal inflammation associated with rhinitis, sinusitis, or rhinosinusitis.

11. The method of claim 10 wherein rhinitis includes acute rhinitis, chronic rhinitis, allergic rhinitis, seasonal allergic rhinitis, perennial allergic rhinitis, vasomotor rhinitis, infectious rhinitis, and atrophic rhinitis.

12. The method of claim 10 wherein the composition is formulated as a nasal spray, nasal drops, nasal droplets, or combinations thereof.

13. The method of claim 10 wherein the composition is nasally administered by a metered dose inhaler (MDI).

14. The method of claim 13 wherein the MDI is any of a breath-actuated MDI, a dry powder inhaler, a spacer/holding chambers in combination with a MDI, and a nebulizer.

15. The method of claim 13 wherein the composition is in a wet spray formulation or a dry spray formulation.

16. The method of claim 10 wherein the composition is nasally administered by a metered dose plunger spray pump.

17. A method of treating at least one of rhinitis, mucosal inflammation associated with rhinitis, sinusitis, rhinosinusitis, and runny nose and stuffy nose symptoms associated with rhinitis, mucosal inflammation associated with rhinitis, sinusitis, or rhinosinusitis in a patient in need of such treatment, the method comprising nasally administering to the patient in need thereof, in a dose regimen effective to treat at least one of rhinitis, mucosal inflammation associated with rhinitis, sinusitis, rhinosinusitis, and runny nose and stuffy nose symptoms associated with rhinitis, mucosal inflammation associated with rhinitis, sinusitis, or rhinosinusitis, a pharmaceutical composition consisting of
a corticosteroid, the corticosteroid formulated with a sufficient concentration of a suspending agent excipient to result in a corticosteroid suspension, the corticosteroid as a free form, pharmaceutically acceptable salt, solvate, bepotastine as a free base, pharmaceutically acceptable salt, solvate at a concentration ranging from 0.5% w/v to 8.00% w/v in aqueous solution;
dibasic sodium phosphate heptahydrate at a concentration of 0.10% w/v to 1.00% w/v;
sodium chloride at a concentration of 0.9% w/v with 0.5% bepotastine, 0.4% w/v with 2.00%-3.00% bepotastine, 0.3% w/v with 4.00% bepotastine, 0.2% w/v with 6.00% bepotastine, 0.1% w/v with 8.00% bepotastine;
edetate disodium at a concentration of 0.005% w/v to 0.100% w/v;
benzalkonium chloride at a concentration of 0.002% w/v to 0.200% w/v; and one of either:

a blend of microcrystalline cellulose and carboxymethyl cellulose at a concentration of 0.5% w/v to 2.5% w/v and polyoxyethylene (20) sorbitan monooleate (polysorbate 80) at a concentration of 0.005% w/v to 0.050% w/v, or hydroxypropylmethylcellulose (HPMC) E15 LV at a concentration of 0.01% w/v to 1.00% w/v, citric acid monohydrate at a concentration of 0.10% w/v to 1.00% w/v, and a taste-masking agent at a concentration of 0.01% w/v to 1.00% w/v.

18. The method of claim 17 wherein the dibasic sodium phosphate heptahydrate is at a concentration of 0.70% w/v, the sodium chloride is at a concentration of 0.30% w/v, the edetate disodium is at a concentration of 0.020% w/v, the benzalkonium chloride is at a concentration of 0.020% w/v, the blend of microcrystalline cellulose and carboxymethyl cellulose is at a concentration of 2.00% w/v and polysorbate 80 is at a concentration of 0.015% w/v, or the HPMC E15 LV is at a concentration of 0.10% w/v, citric acid monohydrate is at a concentration of 0.10% w/v, and sucralose is at a concentration of 0.10% w/v.

19. A method of treating at least one of rhinitis, mucosal inflammation associated with rhinitis, sinusitis, rhinosinusitis, and runny nose and stuffy nose symptoms associated with rhinitis, mucosal inflammation associated with rhinitis, sinusitis, or rhinosinusitis in a patient in need of such treatment, the method comprising nasally administering a pharmaceutical composition consisting essentially of a corticosteroid as a free form, pharmaceutically acceptable salt, or solvate in suspension;

bepotastine as a free base, pharmaceutically acceptable salt, solvate at a concentration ranging from 0.5% w/v to 8.00% w/v in aqueous solution; and at least one of (a) a blend of microcrystalline cellulose and carboxymethyl cellulose, (b) polyoxyethylene (20) sorbitan monooleate (polysorbate 80), and (c) hydroxypropyl methyl cellulose (HPMC)

to the patient in need thereof, in a dose regimen effective to treat at least one of rhinitis, mucosal inflammation associated with rhinitis, sinusitis, rhinosinusitis, and runny nose and stuffy nose symptoms associated with rhinitis, mucosal inflammation associated with rhinitis, sinusitis, or rhinosinusitis.

* * * * *